United States Patent [19]

Tsyrlova et al.

[11] Patent Number: 5,939,391
[45] Date of Patent: Aug. 17, 1999

[54] HEMOGLOBIN ALPHA CHAIN PEPTIDE FRAGMENTS USEFUL FOR INHIBITING STEM CELL PROLIFERATION

[75] Inventors: Irena Tsyrlova, Gaithersburg; Stephen D. Wolpe, Rockville, both of Md.

[73] Assignee: Pro-Neuron, Inc., Rockville, Md.

[21] Appl. No.: 08/535,882

[22] Filed: Sep. 28, 1995

Related U.S. Application Data

[63] Continuation-in-part of application No. 08/316,424, Sep. 30, 1994, which is a continuation-in-part of application No. 08/040,924, Mar. 31, 1993, Pat. No. 5,402,475.

[51] Int. Cl.$^6$ .............................. A61K 37/00; C07K 7/08; C07K 7/50; C07K 14/805
[52] U.S. Cl. ............................ 514/14; 530/326; 530/327; 530/385
[58] Field of Search ..................................... 530/385, 300, 530/326, 327; 514/14

[56] References Cited

U.S. PATENT DOCUMENTS

| | | | |
|---|---|---|---|
| 4,350,683 | 9/1982 | Galfre et al. . | |
| 4,683,194 | 7/1987 | Saiki et al. ................................... | 435/6 |
| 5,028,588 | 7/1991 | Hoffman et al. ............................. | 514/6 |
| 5,239,061 | 8/1993 | Fronticelli et al. ...................... | 530/385 |
| 5,449,759 | 9/1995 | Hoffman et al. .......................... | 530/385 |

FOREIGN PATENT DOCUMENTS

| | | |
|---|---|---|
| 1561261 | 4/1988 | U.S.S.R. . |
| 1614655 | 5/1988 | U.S.S.R. . |
| WO 90/13645 | 11/1990 | WIPO . |
| WO 91/04274 | 4/1991 | WIPO . |
| WO 92/11283 | 7/1992 | WIPO . |
| WO 93/09143 | 5/1993 | WIPO . |

OTHER PUBLICATIONS

Dunlop et al, *Blood*, vol. 79, No. 9, issued May 1, 1992, pp. 2221–2225 "Demonstration of Stem Cell Inhibition and Myeloprotective Effects of SCI/rhMIP1 alpha in vivo".

Davatelis et al, *Journal of Experimental Medicine*, vol. 157, issued Jun. 1988, pp. 1939–1944 "Cloning and Characterization of a cDNA for Murine Macrophage Inflammatory Protein (MIP), a Novel Monokine with Inflammatory and Chemokinetic Properties".

Hunkapillar et al, *Methods in Enzymology*, vol. 91, issued 1983, pp. 227–236 "Isolation of Microgram Quantities of Proteins from Polyacrylamide Gels for Amino Acid Sequence Analysis".

Lathe, *Journal of Molecular Biology*, vol. 183, issued 1985, pp. 1–12, "Synthetic Oligonucleotide Probes Deduced from Amino Acid Sequence Data. Theoretical and Practical Considerations".

Ohtsuka et al, *Journal of Biological Chemistry*, vol. 260, No. 5, issued Mar. 10, 1985, pp. 2605–2608 "An Alternative Approach to Deoxyoligonucleotides as Hybridization Probes by Insertion of Deoxyinosine at Ambiguous Codon Positions".

Kozlov, V.A., et al, *Cell Tissue Kinet.* (1987), 20 485–491, "The effect of haemopoietic stem cell proliferation on the humoral immune response in mice".

Eaves, C.J., et al., *Blood*, V. 78, No. 1 (Jul. 1), 1991:pp. 110–117 "Mechanisms That Regulate the Cell Cycle Status of Very Primitive Hematopoietic Cells in Long–Term Human Marrow Cultures. II. Analysis of Positive and Negative Regulators Produced by Stromal Cells Within the Adherent Layer."

Tejero, C., et al, *Br. J. Cancer* (1984), 50, 335–341 "The cellular specificity of haemopoietic stem cell proliferation regulators."

Graham, G.J., et al., *Nature*, V. 344, Mar. 29, 1990, pp. 442–444 "Identification and characterization of an inhibitor of haemopoietic stem cell proliferation."

Eaves, C.J., et al., *Blood*, vol. 78, No. 1 (Jul. 1), 1991:pp. 110–117 "Mechanisms That Regulate the Cell Cycle Status of Very Primitive Hematopoietic Cells in Long–Term Human marow Cultures. II. Analysis of Positive and Negative Regulators Produced by Stromal Cells Within the Adherent Layer."

Lord, B.I., et al, *British Journal of Haematology*, 1976, 34, 441 "An Inhibitor of Stem Cell Proliferation in Normal Bone Marrow."

Lord, B.I., et al., *Blood Cells* 6.581–593 (1980) "Sources of Haemopoietic Stem Cell Proliferation: Stimulators and Inhibitors."

Graham, G.J., et al, *Nature* vol. 344, Mar. 29, 1990 "Identification and Characterization of an Inhibitor of Haemopoietic Stem Cell Proliferation."

Wolpe, S.D., et al, *J. Exp. Med.* © The Rockefeller University Press, vol. 167, Feb. 1988 570–581 "Macrophages Secrete A Novel Heparin–Binding protein With Inflammatory And Neutrophil Chemokinetic Properties."

Davatelis, G., et al, *Science*, vol. 243, Feb. 24, 1989, 1066–1068 "Macrophage Inflammatory Protein—1:A Prostaglandin–Independent Endogenous Pyrogen."

Broxmeyer, H.E., et al, *J. Exp. Med.* © The Rockefeller University Press, vol. 170, Nov. 1989, 1583–1594 "Myelopoietic Enhancing Effects of Murine Macrophaage Inflammatory Proteins 1 and 2 on Colony Formation In Vitro By Murine And Human Bone Marrow Granulocyte/Macrophage Progenitor Cells."

Mundy, G.R., et al, *Nature*, vol. 275, Sep. 14, 1978 "Loss of Immunoreactivity in Long–Term Bone Marrow Culture."

Eaves, A.C., et al, *CRC Critical Reviews in Oncolong/Hematology*, vol. 7, Issue 2 (1987) 125–138 "Clinical Significance of Long–Term Cultures of Myeloid Blood Cells."

(List continued on next page.)

*Primary Examiner*—Karen C. Carlson
*Attorney, Agent, or Firm*—Nixon & Vanderhye, P.C.

[57] ABSTRACT

Disclosed and claimed are methods for the isolation and use of stem cell inhibiting factors for regulating the abnormal stem cell cycle and for accelerating the post-chemotherapy peripheral blood cell recovery. Also disclosed and claimed are the inhibitors of stem cell proliferation.

7 Claims, 23 Drawing Sheets

OTHER PUBLICATIONS

Eaves, A.C., et al, *The Biology of Hematopoiesis*, Editor: N Daniak, Alan R. Liss, Inc, NY, NY "The Therapeutic Potential of Long–Term CML Marrow Cultures."

Tsyrlova, I.G., et al, *Lukemia: Advances in Biology and Therapy—Progress and Controversies*, S326 (1988) "Improvement of Leukemic LTBMC Establishment by Using Specific Inhibitor of Hematopoietic Stem Cell Proliferation."

Till, J.E., et al, *Radiation Research* 14, 213–222 (1961) "A Direct Measurement of the Radiation Sensitivity of Normal Mouse Bone Marrow Cells."

Becker, A.J., et al, *Blood*, vol. 26, No. 3 (Sep.) 1965, 296–308 "The Effect of Differing Demands for Blood Cell Production on DNA Synthesis by Hemopoietic Colony–Forming Cells of Mice."

Byron, J.W., *Nature*, vol. 228 Dec. 1970, 1204 "Effect of Steroids on the Cycling of Haemopoietic Stem Cells."

Lord, B.I., et al, *The Inhibitors of Hematopoiesis*, vol. 162, pp. 227–239 (1987) "Inhibitor of Haemopoietic CFU–S Proliferation: Assays, Production Sources and Regulatory Mechanisms."

Lord, B.I., et al, *Blood*, vol. 79, No. 10 (May 15) 1992:pp.2605–2609 "Macrophage–Inflammatory Protein protects multipotent hematopoietic Cells From the Cytotoxic Effects of Hydroxyurea In Vivo."

Harrison, D.E., *Blood*, vol. 78, No. 5 (Sep. 2), 1991:pp.1237–1240 "Most Primitive Hematopoietic Stem Cells Are Stimulated To Cycle Rapidly After Treatment With 5–Fluorouracil."

Toksoz, D., et al, *Blood*, vol. 55, No. 6 (Jun.), 1980 "The Regulation of hemopoiesis in Long–term Bone Marrow Cultures. II. Stimulation and Inhibition of Stem Cell Proliferation."

Visser, Jan W.M., et al, *Blood Cells* (1988) 14:369–384 "Isolation of Spleen–Colony Forming Cells (CFU–s) Using Wheat Germ Agglutinin and Rhodamine 123 Labeling."

Whitlock, C., et al, *Ann. Rev. Immunol.* 1985 3:213–35 "In Vitro Analysis of Murine B–Cell Development."

Eaves, A.C., et al, *Blood Cells* (1988) 14:355–368 "Maintenance and proliferation Control of primitive Hemopoietic Progenitors in Long–Term Cultures of human Marrow Cells."

Phillips, G.L., et al, *Bone Marrow Transplantation* (1991), 8, 477–487 "Allogeneic Bone Marrow Transplantation Using Unrelated Donors: A Pilot Study of the Canadian Bone Marrow Transplant Group."

Ignat'Eva O Yu et al, Database Biosis, Biosciences Information Service, Phila., PA, XP002031939, *Abstract; Byull Eksp Biol Med* 98 (9) 1984 (Recd. 1985) 326–329 "Study of the Mechanism of Action of the Stem Cell Inhibition Factor on the Formation of Exogenous Hemopoietic Colonies in the Spleen of Mice".

Golovanova, T.A., et al, *Ontogenez*, 13 (3) 1982 243–250, "Influence of the Factor of Stem Cell Inhibition on the Formation of Hemopoietic Colonies" [English Abstract provided].

Swanson, et al, *Bio/Technology*, vol. 10, pp. 557–559, May 1992, "Production of functional human hemoglobin in transgenic swine".

Kriegler, A.B., et al, *Exp. Hematol.*, vol. 9, No. 1, pp. 11–21, Jan. 1981 "Identification of the "Factor" in Erythrocyte Lystes Which Enhances Colony Growth in Agar Cultures".

Moqattash, S., et al, *Acta Haematol*, 1994; 92:182–186, "Hemopoietic Recovery from AZT Toxicity with Recombinant Hemoglobin in a Murine Model of AIDS".

Petrov, Rem V., et al, *Bioscience Reports*, vol. 15, No. 1, 1995 "Myelopeptides: Bone Marrow Regulatory Mediators".

Shaeffer, J.R., *The Journal of Biological Chemistry*, vol. 269, No. 47, Issue of Nov. 25, 1994, pp. 29530–29536, "Heterogeneity in the Structure of the Ubiquitin Connugates of Human α Globin".

Karelin, A.A., et al, *Peptides*, vol. 16, No. 4, pp. 693–697, 1995 "Proteolytic Degradation of hemoglobin in Erythrocytes Leads to Biologically Active Peptides".

Mueller, S., et al, *Blood*, 1995 Nov. 15;86(10):1974—1974 "Purified Adult Hemoglobin Stimulates the Proliferation and Differentiation of Erythroid Progenitors".

Analysis: Channel A

| Peak No. | Time | Type | Height(μY) | Area(μY-sec) | Area% |
|---|---|---|---|---|---|
| 1 | 4.383 | N1 | 3945 | 95125 | 0.119 |
| 2 | 5.080 | N2 | 28639 | 330889 | 0.413 |
| 3 | 5.216 | N3 | 49084 | 531867 | 0.665 |
| 4 | 7.980 | N1 | 399424 | 1110511 | 1.389 |
| 5 | 8.100 | Err | 1203320 | 2882013 | 3.605 |
| 6 | 8.241 | N3 | 443249 | 1506159 | 1.884 |
| 7 | 8.386 | N4 | 481563 | 2185702 | 2.734 |
| 8 | 8.533 | N5 | 412886 | 1826165 | 2.284 |
| 9 | 8.701 | N6 | 321500 | 842122 | 1.053 |
| 10 | 8.745 | N7 | 404661 | 1610380 | 2.014 |
| 11 | 8.995 | N8 | 435765 | 2489721 | 3.114 |
| 12 | 9.316 | N9 | 517790 | 4801831 | 6.007 |

FIG. 16A

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| Val | Leu | Ser | Pro | Ala | Asp | Lys | Thr | Asn | Val | Lys | Ala | Ala | Trp | Gly | Lys | Val | Gly | Ala | His |
| GTG | CTG | TCT | CCT | GCC | GAC | AAG | ACC | AAC | GTC | AAG | GCC | GCT | TGG | GGT | AAG | GTC | GGC | GCG | CAC |

| 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|
| Ala | Gly | Glu | Tyr | Gly | Ala | Glu | Ala | Leu | Glu | Arg | Met | Phe | Leu | Ser | Phe | Pro | Thr | Thr | Lys |
| GCT | GGC | GAG | TAT | GGT | GCG | GAG | GCC | CTG | GAG | AGg | ATG | TTC | CTG | TCC | TTC | CCC | ACC | ACC | AAG |

| 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|
| Thr | Tyr | Phe | Pro | His | Phe | Asp | Leu | Ser | His | Gly | Ser | Ala | Gln | Val | Lys | Gly | His | Gly | Lys |
| ACC | TAC | TTC | CCG | CAC | TTC | GAC | CTG | AGC | CAC | GGC | TCT | GCC | CAG | GTT | AAG | GGC | CAC | GGC | AAG |

| 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|
| Lys | Val | Ala | Asp | Ala | Leu | Thr | Asn | Ala | Val | Ala | His | Val | Asp | Asp | Met | Pro | Asn | Ala | Leu |
| AAG | GTG | GCC | GAC | GCG | CTG | ACC | AAC | GCC | GTG | GCG | CAC | GTG | GAC | GAC | ATG | CCC | AAC | GCG | CTG |

| 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|
| Ser | Ala | Leu | Ser | Asp | Leu | His | Ala | His | Lys | Leu | Arg | Val | Asp | Pro | Val | Asn | Phe | Lys | Leu |
| TCC | GCC | CTG | AGC | GAC | CTG | CAC | GCG | CAC | AAG | CTT | CCG | GTG | GAC | CCG | GTC | AAC | TTC | AAG | CTC |

| 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|
| Leu | Ser | His | Cys | Leu | Leu | Val | Thr | Leu | Ala | Ala | His | Leu | Pro | Ala | Glu | Phe | Thr | Pro | Ala |
| CTA | AGC | CAC | TGC | CTG | CTG | GTG | ACC | CTG | GCC | GCC | CAC | CTC | CCC | GCC | GAG | TTC | ACC | CCT | GCG |

| 121 | 122 | 123 | 124 | 125 | 126 | 127 | 128 | 129 | 130 | 131 | 132 | 133 | 134 | 135 | 136 | 137 | 138 | 139 | 140 | 141 |
|---|---|---|---|---|---|---|---|---|---|---|---|---|---|---|---|---|---|---|---|---|
| Val | His | Ala | Ser | Leu | Asp | Lys | Phe | Leu | Ala | Ser | Val | Ser | Thr | Val | Leu | Thr | Ser | Lys | Tyr | Arg |
| GTG | CAC | GCC | TCC | CTG | GAC | AAG | TTC | CTG | GCT | TCT | GTG | AGC | ACC | GTG | CTG | ACC | TCC | AAA | TAC | CGT |

FIG. 16B

```
  1           2   3   4   5   6   7   8   9   10  11  12  13  14  15  16  17  18  19  20
  Val         His Leu Thr Pro Glu Glu Lys Ser Ala Val Thr Ala Leu Trp Gly Lys Val Asn Val
  GTG         CAC CTG ACT CCT GAG GAG AAG TCT GCC GTT ACT GCC CTG TGG GGT AAG GTG AAC GTG 21          22  23  24  25  26  27  28  29  30  31  32  33  34  35  36  37  38  39  40
  Asp         Glu Val Gly Gly Glu Ala Leu Gly Arg Leu Leu Val Val Tyr Pro Trp Thr Gln Arg
  GAT         GAA GTT GGT GGT GAG GCC CTG GGC AGg CTG CTG GTG GTC TAC CTT TGG ACC CAG AGG 41          42  43  44  45  46  47  48  49  50  51  52  53  54  55  56  57  58  59  60
  Phe         Phe Glu Ser Phe Gly Asp Leu Ser Thr Pro Asp Ala Val Met Gly Asn Pro Lys Val
  TTC         TTT GAG TCC TTT GGG GAT CTG TCC ACT CCT GAT GCT GTT ATG GGC AAC CCT AAG GTG 61          62  63  64  65  66  67  68  69  70  71  72  73  74  75  76  77  78  79  80
  Lys         Ala His Gly Lys Lys Val Leu Gly Ala Phe Ser Asp Gly Leu Ala His Leu Asp Asn
  AAG         GCT CAT GGC AAG AAA GTG CTC GGT GCC TTT AGT GAT GGC CTG GCT CAC CTC GAC AAC 81          82  83  84  85  86  87  88  89  90  91  92  93  94  95  96  97  98  99  100
  Leu         Lys Gly Thr Phe Ala Thr Leu Ser Glu Leu His Cys Asp Lys Leu His Val Asp Pro
  CTC         AAG GGC ACC TTT GCC ACA CTG AGT GAG CTG CAC TGT GAC AAG CTG CAC GTG GAT CCT 101         102 103 104 105 106 107 108 109 110 111 112 113 114 115 116 117 118 119 120
  Glu         Asn Phe Arg Leu Leu Gly Asn Val Leu Val Cys Val Leu Ala His His Phe Gly Lys
  GAG         AAC TTC AGG CTC CTG GGC AAC GTG CTG GTC TGT GTG CTG GCC CAT CAC TTT GGC AAA 121         122 123 124 125 126 127 128 129 130 131 132 133 134 135 136 137 138 139 140
  Glu         Phe Thr Pro Pro Val Gln Ala Ala Tyr Gln Lys Val Val Ala Gly Val Ala Asn Ala
  GAA         TTC ACC CCA CCA GTG CAG GCT GCC TAT CAG AAA GTG GTG GCT GGT GTG GCT AAT GCC 141         142 143 144 145 146
  Leu         Ala His Lys Tyr His
  CTG         GCC CAC AAG TAT CAC
```

FIG. 16C

```
                  10          20          30          40          50
hHemA.pep    1  V-LSPADKTN VKAAWGKVGA HA-GEYGAEA LERMFLSFP TKTYFPHF          50
hHemB.pep    1  VHLTPEEKSA VTALWGKV-- -NVDEVGGEA LGRLLVVYP WTQRFFESFG         50
mHemA.pep    1  V-LSGEDKSN IKAAWGKIGG HGGAEYGAEA LERMFASFP TKTYFPHF          50
mHemB.pep    1  VHLTDAEKAA VSCLWGKVNS DEVGGEAL   GRLLVVYP WTQRYFDSFG          50
pHemA.pep    1  V-LSAADKAN VKAAWGKVGG QAGAHGAEA LERMFLGFP TKTYFPHF          50
pHemB.pep    1  VHLSAEEKEA VLGLWGKVNV DEVGGEAL   GRLLVVYP WTQRFFESFG         50

60          70          80          90         100
hHemA.pep   51  DLSH----G SAQVKGHGKK VADALTN-- AVAHVDDMPN ALS---ALSDL        100
hHemB.pep   51  DLSTPDAVMG NPKVKAHGKK VLGA-FSD-- GLAHLDNLKG TFA--TLSEL         100
mHemA.pep   51  DVSH----G SAQVKGHGKK VADALAS--  AAGHLDDLPG ALS--ALSDL         100
mHemB.pep   51  DLSSASAIMG NAVKAHGKKV ---ITAFND  GLNHLDSLKG TFASL--SEL        100
pHemA.pep   51  NLSH----G SDQVKAHGQK VADALTK--  AVGHIDDLPG ALS---ALSDL        100
pHemB.pep   51  DLSNADAVMG NPKVKAHGKK V---LQSFSD GLKHLDNLKG TFAXL--SEL        100

110         120         130         140         150
hHemA.pep  101  HAHKLRVDPV NFKLLSHCLL VTLAAHLPAE FTPAVHASLD KFLASVSTV         150
hHemB.pep  101  HCDKLHVDPE NFRLLGNVLV CVLAHHFGKE FTPPVQAAYQ KVVAGVANA         150
mHemA.pep  101  HAHKLRVDPV NFKLLSHCLL VTLASHHPAD FTPAVHASLD KFLASVSTV         150
mHemB.pep  101  HCDKLHVDPE NFRLLGNMTV IVLGHHLGKD FTPAAQAAF- KFLANVSTV         150
pHemA.pep  101  HAHKLRVDPV NFKLLSHCML VTLAAHPDD FNPSVHASLD KFLANVSTV          150
pHemB.pep  101  HCDQLHVDPE NFRLLGNVIV VLARRLGHD FNPDVQAAF- QKVVAGVANA          150

160         170         180         190         200
hHemA.pep  151  LTSKYR....                                                  200
hHemB.pep  151  LAHKYH....                                                  200
mHemA.pep  151  LTSKYR....                                                  200
mHemB.pep  151  LAHKYH....                                                  200
pHemA.pep  151  LTSKYR....                                                  200
pHemB.pep  151  LAHKYH....                                                  200
```

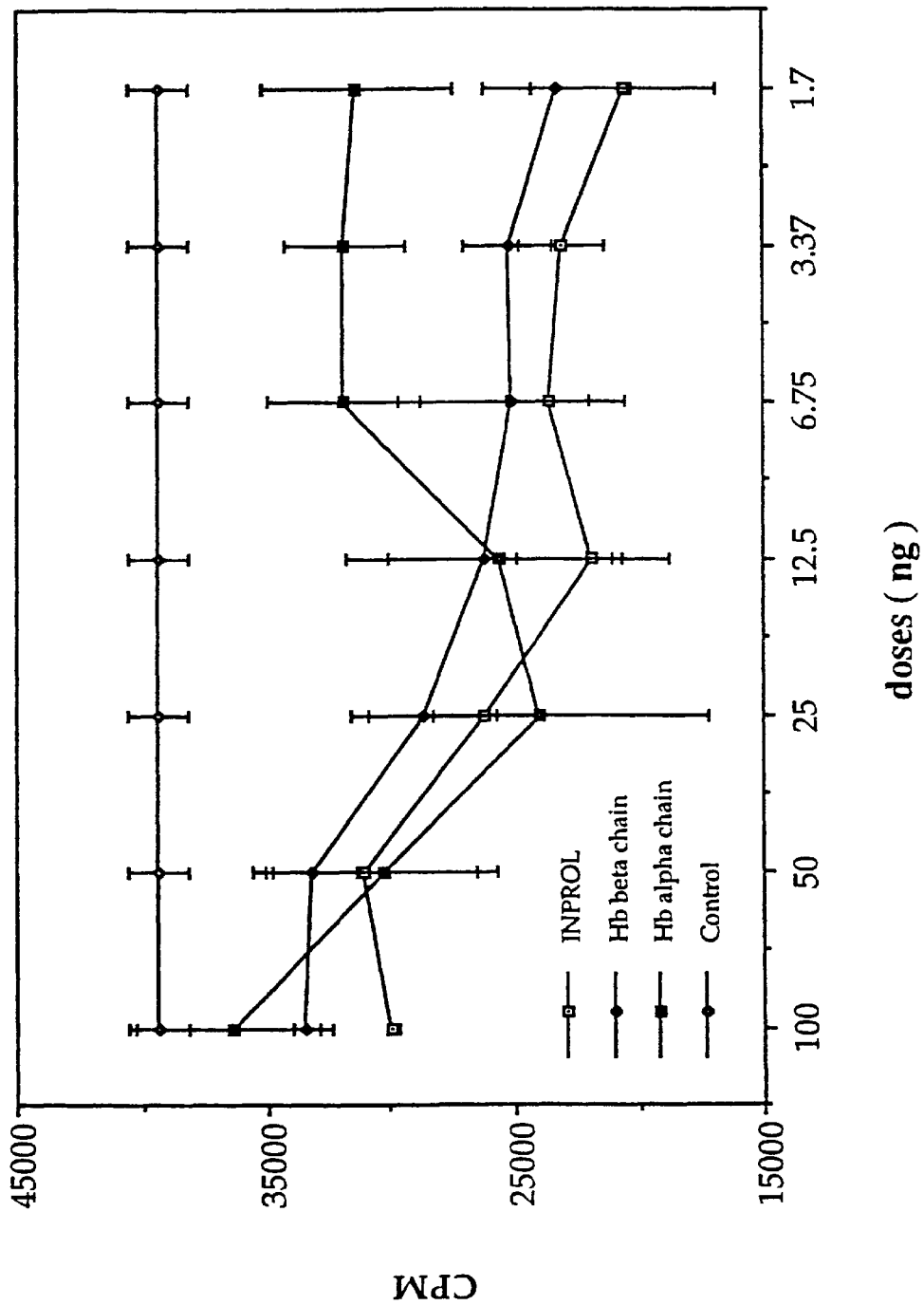

HEMOGLOBIN ALPHA CHAIN PEPTIDE FRAGMENTS USEFUL FOR INHIBITING STEM CELL PROLIFERATION

This application is a continuation-in-part application of U.S. Ser. No. 08/316,424 filed Sep. 30, 1994 which is a continuation-in-part application of U.S. Ser. No. 08/040924 filed Mar. 31, 1993, now U.S. Pat. No. 5,402,475, each of which is hereby incorporated by reference.

FIELD OF THE INVENTION

The present invention relates to the use of inhibitors of stem cell proliferation for regulating stem cell cycle in the treatment of humans or animals having autoimmune diseases, aging, cancer, myelodysplasia, preleukemia, leukemia, psoriasis or other diseases involving hyperproliferative conditions. The present invention also relates to a method of treatment for humans or animals anticipating or having undergone exposure to chemotherapeutic agents, other agents which damage cycling stem cells, or radiation exposure. Finally, the present invention relates to the improvement of the stem cell maintenance or expansion cultures for auto- and allo-transplantation procedures or for gene transfer.

BACKGROUND OF THE INVENTION

Most end-stage cells in renewing systems are short-lived and must be replaced continuously throughout life. For example, blood cells originate from a self-renewing population of multipotent hematopoietic stem cells (HSC). Hematopoietic stem cells are a subpopulation of hematopoietic cells. Hematopoietic cells can be obtained, for example, from bone marrow, umbilical cord blood or peripheral blood (either unmobilized or mobilized with an agent such as G-CSF); hematopoietic cells include the stem cell population, progenitor cells, differentiated cells, accessory cells, stromal cells and other cells that contribute to the environment necessary for production of mature blood cells. Because the hematopoietic stem cells are necessary for the development of all of the mature cells of the hematopoietic and immune systems, their survival is essential in order to reestablish a fully functional host defense system in subjects treated with chemotherapy or other agents.

Hematopoietic cell production is regulated by a series of factors that stimulate growth and differentiation of hematopoietic cells, some of which, for example erythropoietin and G-CSF, are currently used in clinical practice. One part of the control network which has not been extensively characterized, however, is the feedback mechanism that forms the negative arm of the regulatory process (Eaves et al. Blood 78:110–117, 1991).

Early studies by Lord and coworkers showed the existence of a soluble protein factor in normal murine and porcine bone marrow extracts, which was capable of reversibly inhibiting the cycling of HSC (Lord et al., Br. J. Haem. 34:441–446, 1976). This inhibitory activity (50–100 kD molecular weight) was designated stem cell inhibitor (SCI).

Purification of this factor from primary sources was not accomplished due to the difficulties inherent in an in vivo assay requiring large numbers of irradiated mice. In an attempt to overcome these problems Pragnell and co-workers developed an in vitro assay for primitive hematopoietic cells (CFU-A) and screened cell lines as a source of the inhibitory activity (see Graham et al. Nature 344:442–444, 1990).

As earlier studies had identified macrophages as possible sources for SCI (Lord et al. Blood Cells 6:581–593, 1980), a mouse macrophage cell line, J774.2, was selected (Graham et al. Nature 344:442–444, 1990). The conditioned medium from this cell line was used by Graham et al. for purification; an inhibitory peptide was isolated which proved to be identical to the previously described cytokine macrophage inflammatory protein 1-alpha (MIP-1α). Thus, MIP-1α was isolated from a cell line, not from primary material. While Graham et al. observed that antibody to MIP-1α abrogated the activity of a crude bone marrow extract, other workers have shown that other inhibitory activities are important. For example, Graham et al. (J. Exp. Med. 178:925–32, 1993) have suggested that TGFβ, not MIP-1α, is a primary inhibitor of hematopoietic stem cells. Further, Eaves et al. (PNAS 90:12015–19, 1993) have suggested that both MIP-1α and TGFβ are present at sub optimal levels in normal bone marrow and that inhibition requires a synergy between the two factors.

Other workers have described additional stem cell inhibitory factors. Frindel and coworkers have isolated a tetrapeptide from fetal calf marrow and from liver extracts which has stem cell inhibitory activities (Lenfant et al., PNAS 86:779–782, 1989). Paukovits et al. (Cancer Res. 50:328–332, 1990) have characterized a pentapeptide which, in its monomeric form, is an inhibitor and, in its dimeric form, is a stimulator of stem cell cycling. Other factors have also been claimed to be inhibitory in various in vitro systems (see Wright and Pragnell in *Bailliere's Clinical Haematology* v. 5, pp. 723–39, 1992 (Bailliere Tinadall, Paris)).

Tsyrlova et al., SU 1561261 A1, disclosed a purification process for a stem cell proliferation inhibitor.

To date, none of these factors have been approved for clinical use. However, the need exists for effective stem cell inhibitors. The major toxicity associated with chemotherapy or radiation treatment is the destruction of normal proliferating cells which can result in bone marrow suppression or gastrointestinal toxicity. An effective stem cell inhibitor would protect these cells and allow for the optimization of these therapeutic regimens. Just as there is a proven need for a variety of stimulatory cytokines (i.e., cytokines such as IL-1, IL-2, IL-3, IL-4, IL-5, IL-6, IL-7, IL-9, IL-11, IL-13, IL-14, IL-15, G-CSF, GM-CSF, erythropoietin, thrombopoietin, stem cell factor, flk2/flt3 ligand, etc., which stimulate the cycling of hematopoietic cells ) depending upon the clinical situation, so too it is likely that a variety of inhibitory factors will be needed to address divergent clinical needs.

Hemoglobin is a highly conserved tetrameric protein with molecular weight of approximately 64,000 Daltons. It consists of two alpha and two beta chains. Each chain binds a single molecule of heme (ferroprotoporphyrin IX), an iron-containing prosthetic group. Vertebrate alpha and beta chains were probably derived from a single ancestral gene which duplicated and then diverged; the two chains retain a large degree of sequence identity both between themselves and between various vertebrates (see FIG. 16A). In humans, the alpha chain cluster on chromosome 16 contains two alpha genes (alpha$_1$ and alpha$_2$) which code for identical polypeptides, as well as genes coding for other alpha-like chains: zeta, theta and several non-transcribed pseudogenes (see FIG. 16B for cDNA and amino acid sequences of human alpha chain). The beta chain cluster on chromosome 11 consists of one beta chain gene and several beta-like genes: delta, epsilon, G gamma and A gamma, as well as at least two unexpressed pseudogenes (see FIG. 16C for cDNA and amino acid sequences of human beta chain).

The expression of these genes varies during development. In human hematopoiesis, which has been extensively characterized, embryonic erythroblasts successively synthesize tetramers of two zeta chains and two epsilon chains (Gower I), two alpha chains and two epsilon chains (Gower II) or two zeta chains and two gamma chains (Hb Portland). As embryogenesis proceeds, the predominant form consists of fetal hemoglobin (Hb F) which is composed of two alpha chains and two gamma chains. Adult hemoglobin (two alpha and two beta chains) begins to be synthesized during the fetal period; at birth approximately 50% of hemoglobin is of the adult form and the transition is complete by about 6 months of age. The vast majority of hemoglobin (approximately 97%) in the adult is of the two alpha and two beta chain variety (Hb A) with small amounts of Hb F or of delta chain (Hb $A_2$) being detectable.

Heme has been extensively examined with regard to its influences on hematopoiesis (see S. Sassa, Seminars Hemat. 25:312–20, 1988 and N. Abraham et al., Int. J. Cell Cloning 9:185–210, 1991 for reviews). Heme is required for the maturation of erythroblasts; in vitro, hemin (chloroferroprotoporphyrin IX - i.e., heme with an additional chloride ion) increases the proliferation of CFU-GEMM, BFU-E and CFU-E. Similarly, hemin increases cellularity in long-term bone marrow cultures.

I. Chemotherapy and Radiotherapy of Cancer

Productive research on stimulatory growth factors has resulted in the clinical use of a number of these factors (erythropoietin, G-CSF, GM-CSF, etc.). These factors have reduced the mortality and morbidity associated with chemotherapeutic and radiation treatments. Further clinical benefits to patients who are undergoing chemotherapy or radiation could be realized by an alternative strategy of blocking entrance of stem cells into cell cycle thereby protecting them from toxic side effects.

II. Bone Marrow Transplantation

Bone marrow transplantation (BMT) is a useful treatment for a variety of hematological, autoimmune and malignant diseases; current therapies include hematopoietic cells obtained from umbilical cord blood or from peripheral blood (either unmobilized or mobilized with agents such as G-CSF) as well as from bone marrow. Ex vivo manipulation of hematopoietic cells is currently being used to expand primitive stem cells to a population suitable for transplantation. Optimization of this procedure requires: (1) sufficient numbers of stem cells able to maintain long term reconstitution of hematopoiesis; (2) the depletion of graft versus host-inducing T-lymphocytes and (3) the absence of residual malignant cells. This procedure can be optimized by including a stem cell inhibitor(s) for ex vivo expansion.

The effectiveness of purging of hematopoietic cells with cytotoxic drugs in order to eliminate residual malignant cells is limited due to the toxicity of these compounds for normal hematopoietic cells and especially stem cells. There is a need for effective protection of normal cells during purging; protection can be afforded by taking stem cells out of cycle with an effective inhibitor.

III. Peripheral Stem Cell Harvesting

Peripheral blood stem cells (PBSC) offer a number of potential advantages over bone marrow for autologous transplantation. Patients without suitable marrow harvest sites due to tumor involvement or previous radiotherapy can still undergo PBSC collections. The use of blood stem cells eliminates the need for general anesthesia and a surgical procedure in patients who would not tolerate this well. The apheresis technology necessary to collect blood cells is efficient and widely available at most major medical centers. The major limitations of the method are both the low normal steady state frequency of stem cells in peripheral blood and their high cycle status after mobilization procedures with drugs or growth factors (e.g., cyclophosphamide, G-CSF, stem cell factor). An effective stem cell inhibitor would be useful to return such cells to a quiescent state, thereby preventing their loss through differentiation.

IV. Treatment of Hyperproliferative Disorders

A number of diseases are characterized by a hyperproliferative state in which dysregulated stem cells give rise to an overproduction of end stage cells. Such disease states include, but are not restricted to, psoriasis, in which there is an overproduction of epidermal cells, and premalignant conditions in the gastrointestinal tract characterized by the appearance of intestinal polyps. A stem cell inhibitor would be useful in the treatment of such conditions.

V. Gene Transfer

The ability to transfer genetic information into hematopoietic cells is currently being utilized in clinical settings. Hematopoietic cells are a useful target for gene therapy because of ease of access, extensive experience in manipulating and treating this tissue ex vivo and because of the ability of blood cells to permeate tissues. Furthermore, the correction of certain human genetic defects may be possible by the insertion of a functional gene into the primitive stem cells of the human hematopoietic system.

There are several limitations for the introduction of genes into human hematopoietic cells using either retrovirus vectors or physical techniques of gene transfer: (1) The low frequency of stem cells in hematopoietic tissues has necessitated the development of high efficiency gene transfer techniques; and (2) more rapidly cycling stem cells proved to be more susceptible to vector infection, but the increase of the infection frequency by stimulation of stem cell proliferation with growth factors produces negative effects on long term gene expression, because cells containing the transgenes are forced to differentiate irreversibly and lose their self-renewal. These problems can be ameliorated by the use of a stem cell inhibitor to prevent differentiation and loss of self-renewal.

SUMMARY OF THE INVENTION

The present invention relates to polypeptides which are inhibitors of stem cell proliferation ("INPROL") and their use.

The present invention includes an inhibitor of stem cell proliferation characterized by the following properties:

(a) Specific activity ($IC_{50}$) less than or equal to 20 ng/ml in a murine colony-forming spleen (CFU-S) assay (see Example 4), (b) Molecular weight greater than 10,000 and less than 100,000 daltons (by ultrafiltration), (c) Activity sensitive to degradation by trypsin, (d) More hydrophobic than MIP-1α or TGFβ and separable from both by reverse phase chromatography (see Example 12), (e) Biological activity retained after heating for one hour at 37° C., 55° C. or 75° C. in aqueous solution and (f) Biological activity retained after precipitation with 1% hydrochloric acid in acetone.

The present invention is further characterized and distinguished from other candidate stem cell inhibitors (e.g., MIP-1α, TGFβ band various oligopeptides) by its capacity to achieve inhibition in an in vitro assay after a short preincubation period (see Example 5).

The present invention also comprises pharmaceutical compositions containing INPROL for treatment of a variety of disorders.

The present invention provides a method of treating a subject anticipating exposure to an agent capable of killing or damaging stem cells by administering to that subject an effective amount of a stem cell inhibitory composition. The stem cells protected by this method may be hematopoietic stem cells ordinarily present and dividing in the bone marrow. Alternatively, stem cells may be epithelial, located for example, in the intestines or scalp or other areas of the body or germ cells located in reproductive organs. The method of this invention may be desirably employed on humans, although animal treatment is also encompassed by this method. As used herein, the terms "subject" or "patient" refer to an animal, such as a mammal, including a human.

In another aspect, the invention provides a method for protecting and restoring the hematopoietic, immune or other stem cell systems of a patient undergoing chemotherapy, which includes administering to the patient an effective amount of INPROL.

In still a further aspect, the present invention involves a method for adjunctively treating any cancer, including those characterized by solid tumors, by administering to a patient having cancer an effective amount of INPROL to protect stem cells of the bone marrow, gastrointestinal tract or other organs from the toxic effects of chemotherapy or radiation therapy.

Yet another aspect of the present invention involves the treatment of leukemia, comprising treating hematopoietic cells having proliferating leukemia cells therein with an effective amount of INPROL to inhibit proliferation of normal stem cells, and treating the bone marrow with a cytotoxic agent to destroy leukemia cells. This method may be enhanced by the follow-up treatment of the bone marrow with other agents that stimulate its proliferation; e.g., colony stimulating factors. In one embodiment this method is performed in vivo. Alternatively, this method is also useful for ex vivo purging and expansion of hematopoietic cells for transplantation.

In still a further aspect, the method involves treating a subject having any disorder caused by proliferating stem cells. Such disorders, such as psoriasis, myelodysplasia, some autoimmune diseases, immuno-depression in aging, are treated by administering to the subject an effective amount of INPROL to partially inhibit proliferation of the stem cell in question.

The present invention provides a method for reversibly protecting stem cells from damage from a cytotoxic agent capable of killing or damaging stem cells. The method involves administering to a subject anticipating exposure to such an agent an effective amount of INPROL.

The present invention also provides:

An inhibitor of stem cell proliferation isolated from porcine or other bone marrow by the following procedure (see Example 12):

(a) Extraction of bone marrow and removal of particulate matter through filtration, (b) Heat treatment at 56° C. for 40 minutes followed by cooling in ice bath, (c) Removal of precipitate by centrifugation at 10,000 g for 30 minutes at 4° C., (d) Acid precipitation by addition of supernatant to 10 volumes of stirred ice-cold acetone containing 1% by volume concentrated hydrochloric acid and incubation at 4° C. for 16 hours, (e) Isolation of precipitate by centrifugation at 20,000 g for 30 minutes at 4° C. and washing with cold acetone followed by drying, (f) Isolation by reverse phase chromatography and monitoring activity by inhibition of colony formation by bone marrow cells pretreated with 5-fluorouracil and incubated in the presence of murine IL-3, as well as by absorption at 280 nm and by SDS-PAGE.

The present invention also provides:

A method for purifying an inhibitor of stem cell proliferation substantially free from other proteinaceous materials comprising the preceding steps, as also described in more detail below.

The present invention also provides:

A method of treatment for humans or animals wherein an inhibitor of stem cell proliferation functions to ameliorate immunosuppression caused by stem cell hyperproliferation.

The present invention also provides:

A method of treatment for humans or animals wherein said inhibitor of stem cell proliferation is administered after the stem cells are induced to proliferate by exposure to a cytotoxic drug or irradiation procedure. Stem cells are normally quiescent but are stimulated to enter cell cycle after chemotherapy. This renders them more sensitive to a second administration of chemotherapy; the current method protects them from this treatment.

The present invention also provides:

A method of treatment for humans or animals wherein said inhibitor of stem cell proliferation is administered as an adjuvant before or together with vaccination for the purpose of increasing immune response.

The present invention also provides:

A method of treatment for humans or animals receiving cytotoxic drugs or radiation treatment which comprises administering an effective amount of the inhibitor of stem cell proliferation to protect stem cells against damage.

The invention also includes a pharmaceutical composition comprising hemoglobin and a pharmaceutically acceptible carrier.

The invention also includes a pharmaceutical composition comprising (a) a polypeptide selected from the group consisting of the alpha chain of hemoglobin, the beta chain of hemoglobin, the gamma chain of hemoglobin, the delta chain of hemoglobin, the epsilon chain of hemoglobin and the zeta chain of hemoglobin, and (b) a pharmaceutically acceptible carrier. Such pharmaceutical compositions can composed of a single polypeptide selected from said group, a mixture of polypeptides selected from said group or polypeptides from said group in the form of dimers or multimers, with or without heme.

The invention also includes peptides having the sequences:

Phe-Pro-His-Phe-Asp-Leu-Ser-His-Gly-Ser-Ala-Gln-Val (SEQ ID NO:1),

Cys-Phe-Pro-His-Phe-Asp-Leu-Ser-His-Gly-Ser-Ala-Gln-Val-Cys (SEQ ID NO:2)
where the two Cys residues form a disulfide bond, Cys-Phe-Pro-His-Phe-Asp-Leu-Ser-His-Gly-Ser-Ala-Gln-Val-Cys
where the two Cys residues are joined by a carbon bridge, and Asp-Ala-Leu-Thr-Asn-Ala-Val-Ala-His-Val-Asp-Asp-Met-Pro-Asn-Ala-Leu-Ser-Ala (SEQ ID NO:3).

Also included in the invention are DNA sequences encoding the above identified peptides, vectors containing said DNA sequences and host cells containing said vectors. These peptides can be synthesized using standard chemical techniques (e.g., solid phase synthesis) or by using recombinant techniques (e.g., fusion systems such as those employing glutathione-S-transferase (D. B. Smith and K. S.

Johnson, Gene 67:31–40, 1988), thioredoxin (LaVallie et al., Biotechnology 11:187–193, 1993) or ubiquitin (Butt et al., PNAS 86:2540–4, 1989; U.S. Pat. No. 5,391,490)).

Additionally the invention includes a method of inhibiting stem cell proliferation comprising contacting hematopoietic cells with a compound capable of binding opiate receptors, advantageously the mu subclass of opiate receptors. Peptides (called "hemorphins") have been isolated from hemoglobin which exhibit opiate-like activities (e.g., Brantl et al., Eur. J. Pharm, 125:309–10, 1986; Davis et al. Peptides 10:747–51, 1989; Karelin et al. Bioch. Biophys. Res. Comm, 202:410–5, 1994; Zhao et al., Ann. N.Y. Acad. Sci 750:452–8, 1995). Each of these articles is hereby incorporated by reference.

The invention also includes a method of inhibiting stem cell proliferation comprising contacting hematopoietic cells with a peptide selected from the group of hemorphin peptides having the sequence:

Leu-Val-Val-Tyr-Pro-Trp-Thr-Gin-Arg-Phe, (SEQ ID NO:4)

Leu-Val-Val-Tyr-Pro-Trp-Thr-Gln-Arg, (SEQ ID NO:5)

Leu-Val-Val-Tyr-Pro-Trp-Thr-Gln, (SEQ ID NO:6)

Leu-Val-Val-Tyr-Pro-Trp-Thr, (SEQ ID NO:7)

Leu-Val-Val-Tyr-Pro-Trp, (SEQ ID NO:8)

Leu-Val-Val-Tyr-Pro, (SEQ ID NO:9)

Val-Val-Tyr-Pro-Trp-Thr-Gln, (SEQ ID NO:10)

Tyr-Pro-Trp-Thr-Gln-Arg-Phe, (SEQ ID NO:11)

Tyr-Pro-Trp-Thr-Gln-Arg, (SEQ ID NO:12)

Tyr-Pro-Trp-Thr-Gln, and (SEQ ID NO:13)

Tyr-Pro-Trp-Thr.

The above peptides have sequence similarity to other opiate-like peptides such as those of the Tyr-MIF-1 family (see Reed et al., Neurosci. Biobehav. Rev. 18:519–25, 1994 for review), the casein-derived casomorphins (Brantl et al., Hoppe-Seyler's Z. Physiol. Chem. 360:1211–16, 1979; Loukas et al., Biochem. 22:4567–4573, 1983; Fiat and Jolles, Mol. Cell. Biochem. 87:5–30, 1989), peptides derived from cytochrome b, termed cytochrophins (Brantl et al., Eur. J. Pharm. 111:293–4, 1985) as well as peptides derived from combinatorial libraries screened for binding to opiate receptors (see Dooley et al., Peptide Research 8:124–137, 1995 for review). Each of these articles is hereby incorporated by reference.

The invention also includes a method of inhibiting stem cell proliferation comprising contacting hematopoietic cells with a peptide selected from the group consisting of Tyr-MIF-1 related peptides, casomorphins and cytochrophins. Specifically included are the Tyr-MIF-1 peptides having the sequences:

Tyr-Pro-Try-Gly-NH$_2$,

Tyr-Pro-Lys-Gly-NH$_2$,

Tyr-Pro-Leu-Gly-NH$_2$, and

Pro-Leu-Gly-NH$_2$.

The invention also includes a method of conducting gene therapy in a mammal comprising:

a) removing hematopoietic cells from said mammal, b) optionally treating said hematopoietic cells ex vivo with at least one stimulatory cytokine to induce stem cell proliferation, c) transfecting said hematopoietic cells with a predetermined gene, d) contacting said transfected hematopoietic cells ex vivo with INPROL, e) transplanting into a mammal the hematopoietic cells of step d, f) optionally treating said mammal in vivo with INPROL.

The invention also includes a method of conducting ex vivo stem cell expansion comprising treating said hematopoietic cells with INPROL and at least one stimulatory cytokine. INPROL is contacted with the hematopoietic cells before, during and/or after contact with the stimulatory cytokine.

The invention also includes a pharmaceutical composition comprising (a) INPROL and (b) at least one inhibitory compound selected from the group consisting of MIP-1α, TGFβ, TNFα, INFα, INFβ, INFγ, the pentapeptide pyroGlu-Glu-Asp-Cys-Lys, (SEQ ID NO;14) the tetrapeptide N-Acetyl-Ser-Asp-Lys-Pro, and the tripeptide glutathione (Gly-Cys-γGlu).

The invention also includes a pharmaceutical composition comprising (a) INPROL and (b) at least one stimulatory compound selected from the group consisting of IL-1, IL-2, IL-3, IL-4, IL-5, IL-6, IL-7, IL-9, IL-11, IL-13, IL-14, IL-15, G-CSF, GM-CSF, M-CSF, erythropoietin, thrombopoietin, stem cell factor, and flk2/flt3 ligand.

The current invention describes an inhibitor of stem cells (INPROL) which is different from those known in the art such as MIP-1α, TGFβ, the tetrapeptide of Frindel and colleagues or the pentapeptide of Paukovits and coworkers (cf., Wright & Pragnell, 1992 (op cit)). Naturally occuring INPROL has a molecular weight exceeding 10,000 daltons by ultrafiltration which distinguishes it from the tetrapeptide as well as the pentapeptide. It is more hydrophobic than MIP-1α or TGFβ, in reverse phase chromatography systems, distinguishing it from those cytokines. Further, its mode of action is different from that of any previously described inhibitor in that it is active in an in vitro assay when used during a preincubation period only. MIP-1α for example, is not effective when used during a preincubation period only (Example 5). Further, naturally occuring INPROL is active in an assay measuring "high proliferative potential cells" (HPP-PFC) whereas MIP-1α is not (Example 6).

BRIEF DESCRIPTION OF THE DRAWINGS

FIG. 1—Lane 1 is chymotrypsinogen, Lane 2 is ovalbumin, Lane 3 is BSA, Lane 4 is fractions <30 kD, Lane 5 is fractions 30–50 kD and Lane 6 is fractions 50–100 kD.

FIG. 2—Lane 1 is after ammonium sulfate precipitation (40–80%) and lanes 2–5 are DEAE fractions (Lane #2 represents the active fraction).

FIG. 3—Lane 1 is the supernatant after ammonium sulfate precipitation, Lane 2 is the active DEAE fraction, Lanes 3–5 represent gel filtration fractions (lane #5 represents the active fraction)

FIG. 4—Lane 2 represents the final product.

FIG. 16 shows hemoglobin sequences: FIG. 16A shows the cDNA (SEQ ID NO:15) and amino acid (SEQ ID NO:16) sequences of human alpha hemoglobin and FIG. 16B shows the cDNA (SEQ ID NO:17) and amino acid (SEQ ID NO:18) sequences of human beta hemoglobin. Numbering is according to the amino acid. FIG. 16C shows an amino acid sequence comparison of the alpha and beta chains of human, (SEQ ID NO:16 and SEQ ID NO:18) murine (SEQ ID NO:19 and SEQ ID NO:20) and porcine (SEQ ID NO:21 and SEQ ID NO:22) hemoglobins.

FIG. 20 shows a comparison of the effects of purified pig alpha hemoglobin, beta hemoglobin or pINPROL in the FDCP-MIX assay.

Figure 1:
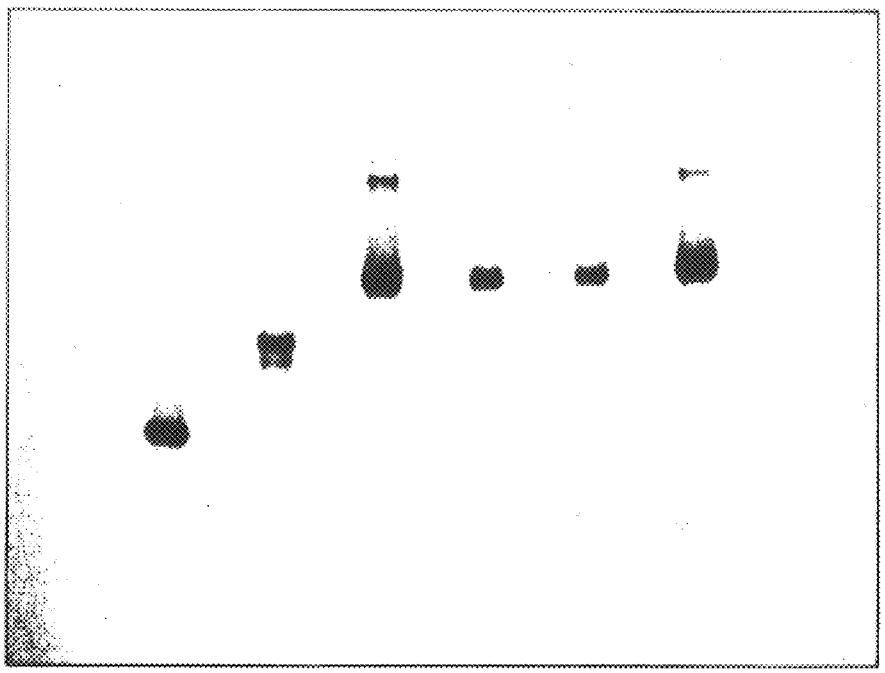
FIGS. 1–4 show an SDS polyacrylamide gel run of the product after each stage of purification.

In order that the invention herein described may be more fully understood, the following detailed description is set forth. This description, while exemplary of the present invention, is not to be construed as specifically limiting the invention and such variations which would be within the purview of one skilled in this art are to be considered to fall within the scope of this invention.

DETAILED DESCRIPTION OF THE PREFERRED EMBODIMENTS

INPROL reversibly inhibits division of stem cells. Specifically, INPROL is effective in temporarily inhibiting cell division of hematopoietic stem cells. Thus, the method of this invention may be employed in alleviating the undesirable side effects of chemotherapy on the patient's hematopoietic, myeloid and immune systems by protecting stem cells from damage caused by chemotherapeutic agents or radiation used to destroy cancer or virally infected cells. In one embodiment of the invention, INPROL is administered to the patient in a dosage sufficient to inhibit stem cell division while the chemotherapeutic agent acts on diseased cells. After the chemotherapeutic agent has performed its function, the stem cells inhibited by INPROL will, without further treatment, revert to dividing cells. If it is desired to enhance the regeneration of hematopoiesis, stimulatory growth factors or cytokines may be used in addition.

As used herein, the term "INPROL" includes mammalian proteins, purified as in the Examples, hemoglobin, the alpha chain of hemoglobin (with or without the heme group), the beta chain of hemoglobin (with or without the heme group), mixtures of alpha and beta chains (with or without the heme group), and fragments or analogs of these proteins including embryonic, fetal or adult forms (e.g., alpha, beta, gamma, delta, epsilon or zeta chains, either alone or as mixtures, dimers or multimers, with or without the heme group) having the ability to inhibit stem cell proliferation. The term "INPROL" includes naturally occurring as well as non-naturally occurring (e.g., recombinantly produced) forms of these proteins.

In a typical clinical situation, INPROL is administered to a patient in a daily regimen by intravenous injection or infusion in dosage unit form using, for example, 0.01 to 100 mg/kg, advantageously 0.1 to 1.0 mg/kg, of INPROL administered, e.g., 4 to 60 hours prior to standard chemotherapy or radiation treatments.

In another embodiment of the invention, pretreatment with INPROL allows for increased doses of chemotherapeutic agents or of radiation beyond doses normally tolerated in patients.

A large fraction of hematopoietic stem cells are normally quiescent (non-cycling). However, as a compensatory response to chemotherapy-induced hematopoietic damage, a larger proportion of stem cells enter into cycling after chemotherapy, which makes them particularly vulnerable to subsequent doses of cytotoxic chemotherapy or therapeutic irradiation. By inhibiting cycling of such stem cells, INPROL treatment permits earlier or more frequent administration of subsequent doses of cytotoxic chemotherapy, either at conventional or elevated doses.

In one embodiment of the invention, INPROL (0.1 mgs. to 6 gms - advantageously 1.0 to 60 mgs.) is administered about 24 hours to 10 days after an initial dose of chemotherapy. After another 4 to 60 hours, advantageously 24 to 48 hours, another dose of chemotherapy is administered. This cycle of alternating chemotherapy and INPROL is continued according to therapeutic benefit. Chemotherapy agents and protocols for administration are selected according to suitability for particular tumor types in standard clinical practice. Optionally, stimulatory growth factors such as G-CSF, stem cell factor, are used after chemotherapy or radiation treatment to further improve hematopoietic reconstitution.

For ex vivo applications 0.1 ng to 100 ng/$10^6$ cells/ml, advantageously 20–50 ng/$10^6$ cells/ml, of INPROL are used.

In another embodiment of the invention, INPROL is employed in a method for preparing autologous hematopoietic cells for transplantation. The hematopoietic cells are treated ex vivo with an effective amount of INPROL to inhibit stem cell division and then purged of cancerous cells by administering to the marrow cultures an effective amount of a chemotherapeutic agent or radiation. Chemotherapy agents with specificity for cycling cells are preferred. Marrow thus treated is reinjected into the autologous donor. Optionally, the patient is treated with an agent known to stimulate hematopoiesis to improve the hematopoietic reconstitution of the patient.

In another embodiment of the invention, INPROL is employed as an adjunctive therapy in the treatment of leukemia. For example, in disease states where the leukemic cells do not respond to INPROL, the leukemic hematopoietic cells cells are treated ex vivo with INPROL. The proliferation of normal stem cells is prevented by administration of INPROL. Thus, during the time that the proliferating leukemic cells are treated with a cell cycle-specific cytotoxic agent, a population of normal stem cells is protected from damage. Additionally, a stimulatory cytokine, such as IL-3 or GM-CSF, is optionally administered to induce cycling in the leukemic cells during drug or radiation treatment while the normal stem cells are protected with INPROL. The patient is treated with chemotherapy agents or radiation to destroy leukemic cells, and the purged marrow is then transplanted back into the patient to establish hematopoietic reconstitution.

Similarly, in another embodiment of the invention for treatment of patients with serious viral infections that involve blood cells or lymphocytes, such as HIV infection, hematopoietic cells are treated ex vivo with INPROL followed by antiviral agents, drugs which destroy infected cells, or antibody-based systems for removing infected cells. Following myeloablative antiviral or myeloablative chemotherapy to eradicate viral host cells from the patient, the INPROL-treated marrow cells are returned to the patient.

In another embodiment of the invention, INPROL is employed to treat disorders related to hyperproliferative stem cells. For example, psoriasis is a disorder caused by hyperproliferating epithelial cells of the skin and is sometimes treated with cytotoxic drugs. Other pre-neoplastic lesions in which stem cell proliferation is involved are also amenable to effective amounts of INPROL employed to inhibit wholly or partially the proliferation of the stem cells. For these uses, topical or transdermal delivery compositions (e.g., ointments, lotions, gels or patches) containing INPROL are employed where appropriate, as an alternative to parenteral administration. In most cases of leukemia, the leukemia progenitors are differentiated cell populations which are not affected by INPROL and which are therefore treated by methods using INPROL such as those described above. In cases where leukemia progenitors are very primitive and are directly sensitive to inhibition by INPROL, proliferation of leukemia cells is attenuated by administration of effective amounts of INPROL.

Antibodies, monoclonal or polyclonal, are developed by standard techniques to the INPROL polypeptides. These antibodies or INPROL polypeptides are labeled with detectable labels of which many types are known in the art. The labeled INPROL or anti-INPROL antibodies are then employed as stem cell markers to identify and isolate stem cells by administering them to a patient directly for diagnostic purposes. Alternatively, these labeled polypeptides or antibodies are employed ex vivo to identify stem cells in a hematopoietic cell preparation to enable their removal prior to purging neoplastic cells in the marrow. In a similar manner, such labeled polypeptides or antibodies are employed to isolate and identify epithelial or other stem cells. In addition, such antibodies, labeled or unlabeled, are used therapeutically through neutralization of INPROL activity or diagnostically through detection of circulating INPROL levels.

INPROL can be cloned from human gene or cDNA libraries for expression of recombinant human INPROL using standard techniques. For example, using sequence information obtained from the purified protein, oligonucleotide probes are constructed which can be labeled, e.g., with 32-phosphorus, and used to screen an appropriate cDNA library (e.g., from bone marrow). Alternatively, an expression library from an appropriate source (e.g., bone marrow) is screened for cDNA's coding for INPROL using antibody or using an appropriate functional assay (e.g., that described in Example 2). Hemoglobin itself, as well as the individual alpha and beta chains, have been cloned and expressed using methods known in the state of the art (see Pagnier et al., Rev. Fr. Transfus. Hemobiol. 35:407–15, 1992; Looker et al., Nature 356:258–60, 1992; Methods in Enzymology vol. 231, 1994). Each of these articles is hereby incorporated by reference.

The present invention includes DNA sequences which include: the incorporation of codons "preferred" for expression by selected nonmammalian hosts: the provision of sites for cleavage by restriction endonuclease enzymes; and the provision of additional initial, terminal or intermediate DNA sequences which facilitate construction of readily-expressed vectors or production or purification of the alpha, beta, gamma, delta, epsilon and/or zeta chain of hemoglobin.

The present invention also provides DNA sequences coding for polypeptide analogs or derivatives of hemoglobin alpha, beta, gamma, delta, epsilon and/or zeta chains which differ from naturally-occurring forms in terms of the identity or location of one or more amino acid residues (i.e., deletion analogs containing less than all of the residues specified; substitution analogs, wherein one or more residues specified are replaced by other residues; and addition analogs wherein one or more amino acid residues is added to a terminal or medial portion of the polypeptide) and which share some or all of the properties of naturally-occurring forms.

In an advantageous embodiment, INPROL is the product of prokaryotic or eukaryotic host expression (e.g., by bacterial, yeast, higher plant, insect and mammalian cells in culture) of exogenous DNA sequences obtained by genomic or cDNA cloning or by gene synthesis. That is, in an advantageous embodiment, INPROL is "recombinant INPROL". The product of expression in typical yeast (e.g., *Saccharomyces cerevisiae*) or prokaryote (e.g., *E. coli*) host cells are free of association with any mammalian proteins. The products of expression in vertebrate (e.g.,non-human mammalian (e.g., COS or CHO) and avian) cells are free of association with any human proteins. Depending upon the host employed, polypeptides of the invention may be glycosylated or may be non-glycosylated. Polypeptides of the invention optionally also include an initial methionine amino acid residue (at position −1).

The present invention also embraces other products such as polypeptide analogs of the alpha, beta, gamma, delta, epsilon and/or zeta chain of hemoglobin. Such analogs include fragments of the alpha, beta, gamma, delta, epsilon and/or zeta chain of hemoglobin. Following well known procedures, one can readily design and manufacture genes coding for microbial expression of polypeptides having primary sequences which differ from that herein specified for in terms of the identity or location of one or more residues (e.g., substitutions, terminal and intermediate additions and deletions). Alternatively, modifications of cDNA and genomic genes can be readily accomplished by well-known site-directed mutagenesis techniques and employed to generate analogs and derivatives of the alpha, beta, gamma, delta, epsilon or zeta chains of hemoglobin. Such products share at least one of the biological properties of INPROL but may differ in others. As examples, products of the invention include the alpha, beta, gamma, delta, epsilon or zeta chains which is foreshortened by e.g., deletions; or those which are more stable to hydrolysis (and, therefore, may have more pronounced or longer-lasting effects than naturally-occurring); or which have been altered to delete or to add one or more potential sites for O-glycosylation and/or N-glycosylation or which have one or more cysteine residues deleted or replaced by, e.g., alanine or serine residues and are more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within the alpha, beta, gamma, delta, epsilon or zeta chains which fragments may possess one property of INPROL (e.g., receptor binding) and not others (e.g., stem cell inhibitory activity). It is noteworthy that activity is not necessary for any one or more of the products of the invention to have therapeutic utility (see, Weiland et al., Blut 44:173–5, 1982) or utility in other contexts, such as in assays of inhibitory factor antagonism. Competitive antagonists are useful in cases of overproduction of stem cell inhibitors or its receptor.

In addition, peptides derived from the protein sequence which retain biological activity can be chemically synthesized using standard methods. The present invention also provides for sequences coding for peptide analogs or derivatives of hemoglobin alpha, beta, gamma, delta, epsilon and/or zeta chain which differ from naturally-occurring forms in terms of the identity or location of one or more amino acid residues (e.g., deletion analogs containing less than all of the residues specified; substitution analogs, wherein one or more residues specified are replaced by other residues, either naturally occuring or other analogs known in the state of the art such as D-amino acids; and addition analogs wherein one or more amino acid residues is chemically modified to increase stability, solubility and/or resistance to proteolysis) and which share some or all of the properties of naturally-occurring forms.

Peptide sequences such as described above can be identified by a variety of means. Comparison of the three dimensional structures of native hemoglobin chains active in the assay (e.g., alpha chain) with structurally related proteins which are inactive (e.g., myoglobin) can identify regions which have different conformations in three-dimensional space and which are therefore candidate regions for active peptides. Another approach uses selective proteolysis, in which proteolytic enzymes are used in limited digests of hemoglobin chains resulting in peptides which can separated, for example, by reverse phase HPLC and then assayed for stem cell inhibition. Peptides can also be generated by chemical synthesis (e.g., solid phase synthesis); a series of overlapping peptides (e.g., 15-mers) which encompass the sequence of the hemoglobin chain of interest (e.g., alpha chain) can easily be generated and tested in stem cell assays. Combinatorial libraries can be generated in which multiple chemical syntheses are conducted and where selected amino acid positions are made variable resulting in large numbers of peptide analogs for screening (e.g., Dooley et al., Peptide Research 8:124–137, 1995). Alternatively, recombinant methods can be employed. Site directed mutagenesis can be used to identify critical residues necessary for activity of a particular hemoglobin chain. Regions of a chain which is known to be active as a stem cell inhibitor (e.g., alpha chain) can be substituted with regions from a related but inactive protein (e.g., myoglobin) and tested in stem cell assays, allowing for identification of regions necessary for activity. Such identified regions can be expressed as peptides and tested for activity in stem cell cycling assays.

Homologous or analogous versions of INPROL from other species are employed in various veterinary uses, similar to the therapeutic embodiments of the invention described above.

INPROL acts on cycling stem cells by reversibly placing them in an undividing "resting" state. When it is desirable to stimulate the quiescent stem cells into division, e.g., after treatment of a patient with cancer chemotherapy agents or radiation, colony-stimulating factors and other hematopoietic stimulants are administered to the subject. Examples of such factors include but are not limited to: M-CSF (CSF-1), GM-CSF, G-CSF, Megakaryocyte-CSF, thrombopoieitin, stem cell factor or other cytokines, such as IL- 1, IL-2, IL-3, IL-4, IL-5, IL-6, IL-7, IL-9, IL-11, IL-12, IL- 13, IL- 14, or erythropoietin .

INPROL polypeptides or active fragments having stem cell inhibitory activity are purified or synthesized by conventional chemical processes combined with appropriate bioassays for stem cell inhibitory activity, as exemplified in the protocols described below.

In one embodiment of the invention, a therapeutically effective amount of the INPROL protein or a therapeutically effective fragment thereof is employed in admixture with a pharmaceutically acceptable carrier. This INPROL composition is generally administered by parenteral injection or infusion. Subcutaneous, intravenous, or intramuscular injection routes are selected according to therapeutic effect achieved.

When systemically administered, the therapeutic composition for use in this invention is in the form of a pyrogen-free, parenterally acceptable aqueous solution. Pharmaceutically acceptable sterile protein solution, having due regard to pH, isotonicity, stability, carrier proteins and the like, is within the skill of the art.

Also comprehended by the invention are pharmaceutical compositions comprising therapeutically effective amounts of polypeptide products of the invention together with suitable diluents, preservatives, solubilizers, emulsifiers, adjuvants and/or carriers useful in INPROL therapy. A "therapeutically effective amount" as used herein refers to that amount which provides a therapeutic effect for a given condition and administration regimen. Such compositions are liquids, gels, ointments, or lyophilized or otherwise dried formulations and include diluents of various buffer content (e.g., Tris-HCl, acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc. or into liposomes, niosomes, microemulsions, micelles, unilamellar or multilamellar vesicles, biodegradable injectable microcapsules or microspheres, or protein matrices, erythrocyte ghosts, spheroplasts, skin patches, or other known methods of releasing or packaging pharmaceuticals. Such compositions will influence the physical state, solubility, stability, rate of in vivo release, and rate of in vivo clearance of INPROL. Controlled or sustained release compositions include formulation in lipophilic depots (e.g., fatty acids, waxes, oils). Also comprehended by the invention are particulate compositions coated with polymers (e.g., poloxamers or poloxamines) and INPROL coupled to antibodies directed against tissue-specific receptors, ligands or antigens or coupled to ligands of tissue-specific receptors. Other embodiments of the compositions of the invention incorporate particulate forms of protective coatings, protease inhibitory factors or permeation enhancers for various routes of administration, including parenteral, pulmonary, nasal, topical (skin or mucosal) and oral. In another embodiment, the composition containing INPROL is administered topically or through a transdermal patch.

In one embodiment, the compositions of the subject invention are packaged in sterile vials or ampoules in dosage unit form.

The invention also comprises compositions including one or more additional factors such as chemotherapeutic agents (e.g., 5-fluorouracil (5FU), cytosine arabinoside, cyclophosphamide, cisplatin, carboplatin, doxyrubicin, etoposide, taxol, alkylating agents), antiviral agents (e.g., AZT, acyclovir), TNF, cytokines (e.g., interleukins), antiproliferative drugs, antimetabolites, and drugs which interfere with DNA metabolism.

The dosage regimen involved in a method for treating the subject anticipating exposure to such cytotoxic agents or for treatment of hyperproliferating stem cells is determined by the attending physician considering various factors which modify the action of drugs; e.g., the condition, body weight, sex, and diet of the patient, the severity of any infection, time of administration and other clinical factors.

Following the subject's exposure to the cytotoxic agent or radiation, the therapeutic method of the present invention optionally employs administering to the subject one or more lymphokines, colony stimulating factors or other cytokines, hematopoietins, interleukins, or growth factors to generally stimulate the growth and division of the stem cells (and their descendants) inhibited by the prior treatment with INPROL. Such therapeutic agents which encourage hematopoiesis include IL1, IL2, IL-3, IL-4, IL-5, IL-6, IL-7, Meg-CSF, M-CSF (CSF-1), GM-CSF, G-CSF or erythropoietin. The dosages of these agents are selected according to knowledge obtained in their use in clinical trials for efficacy in promoting hematopoietic reconstitution after chemotherapy or hematopoietic stem cell transplant. These dosages would be adjusted to compensate for variations in the physical condition of the patient, and the amount and type of chemotherapeutic agent or radiation to which the subject was exposed. Progress of the reversal of the inhibition of the stem cells caused by administration of INPROL in the treated patient is monitored by conventional methods.

In the treatment of leukemia, it is beneficial to administer both INPROL to inhibit normal stem cell cycling and a stimulator of leukemic cell growth, such as IL-3 or GM-CSF, simultaneously with the cytotoxic drug treatment or during irradiation. By this protocol, it is possible to achieve the greatest differences between the cycling statuses and drug sensitivities of normal and leukemic cells.

EXAMPLE 1

In Vivo Stem Cell Proliferation Inhibition Assay

For the detection of stem cells proliferation the number of CFU-S in S-phase of the cell cycle was measured by the $^3$H-Thymidine "suicide" method (Becker et al., Blood 26:296–308, 1965).

Immature hematopoietic progenitors—Colony Forming Units in spleen (CFU-S)—can be detected in vivo by forming macroscopic colonies in the spleens of lethally irradiated mice, 8–12 days after the intravenous injection of hematopoietic cells (Till & McCulloch, 1961).

For the standard CFU-S proliferation assay the method of $^3$H-Thymidine "suicide" is usually applied (Becker et al., 1965). The method is based on incorporation of radiolabelled Thymidine, ($^3$H-Thymidine) a precursor of DNA into cells during DNA synthesis. The CFU-S which are in S-phase of the cycle at the time of testing, are killed by the high radioactivity and therefore not able to form colonies in spleen. Thus, the difference between the number of CFU-S formed by the injection of the cell sample incubated without $^3$H-Thymidine and the same cells incubated with $^3$H-Thymidine shows the percentage of the proliferating CFU-S in the original sample.

The inhibitor testing can not be done with the bone marrow stem cell population from unstimulated animals, as far as the inhibitor only effects cycling CFU-S, which are as low as 7–10% of the total CFU-S population in the bone marrow of normal mice.

To stimulate CFU-S proliferation, phenylhydrazine (PHZ), or sublethal irradiation were used (Lord, 1976).

We have developed the method of using testosterone-propionate (TSP) based on its stimulatory effect on CFU-S cycling (Byron et al., Nature 228:1204, 1970) which simplified the testing and did not cause any side effects. The TSP induced stimulation of CFU-S proliferation within 20–24 hours after injection and the effect could be seen for at least 7 days.

The procedure used for the screening of the fractions during purification of the Inhibitor was as follows:

Mice: $BDF_1$ or $CBF_1$, mice strains were used throughout all testing.

Donor mice were treated with a 10 mg/100 g dose of TSP by intraperitoneal injection of 0.2 ml/mouse in order to induce 30–35% of the CFU-S into S-phase.

Twenty-four hours later the bone marrow is taken from the femurs for the cell suspension preparation. Five to ten million cells per ml are then incubated with different control and test fractions for 3.5 hours at 37° C. in water bath, with two tubes for each group (one for hot (radioactive) and one for cold (non-radioactive)).

After 3.5 hours, $^3$H-Thymidine (1 mCi/ml, specific activity 18–25 Ci/mmole) is added to each hot tube in a volume of 200 µl per 1 ml of cell suspension; nothing is added to the cold tubes. Incubation is continued for 30 more minutes at 37° C.

After the 30 minute incubation, the kill reaction is terminated by adding 10 ml of cold (4° C.) medium containing 400 μg/ml nonradioactive Thymidine. Cells are washed extensively (3 times).

Cells are resuspended and diluted to a desirable concentration for the injections, usually 2–4×10$^4$ cells per mouse in 0.3–0.5 ml.

Recipient mice, 8–10 per group, are irradiated not later than 6 hours before the injections.

Recipient spleens are harvested on day 9–12 and fixed in Tellesnitsky's solution; the colonies are scored by eye score. The percentage of cells in S-phase are calculated using the formula.

$$\% S = \frac{a-b}{a} \times (100\%)$$

where a—CFU-S number without $^3$H-Thymidine where b—CFU-S number with $^3$H-Thymidine The test data of INPROL presented in Table 1 demonstrate that cycling stem cells after treatment with INPROL become resistant to the action of $^3$H-Thymidine. For this and all of the following examples, the term "pINPROL" refers to the purified protein from porcine bone marrow. The same protection is seen for the S-phase specific cytotoxic drugs cytosine arabinoside and hydroxyurea (data not shown). If the treated stem cells are then washed with the cold media containing non-radioactive Thymidine, the surviving stem cells proliferate in mouse spleens to form colonies normally.

TABLE 1

Inhibitory Activity Of pINPROL On CFU-S Proliferation During Four Hour Incubation With Bone Marrow Cells

| Group | −$^3$H-TdR | +$^3$H-TdR | Percent CFU-S Killed by $^3$H-TdR |
|---|---|---|---|
| No incubation | 22.2 ± 2.0* | 13.7 ± 2.4* | 38.3 ± 1.7 |
| 4 Hour with Media | 18.7 ± 3.0* | 11.4 ± 1.3* | 43.1 ± 1.4 |
| 4 Hour with pINPROL | 21.2 ± 2.3* | 20.7 ± 2.6* | 2.1 ± 0.08 |

*CFU-S per 2 × 10$^4$ cells

EXAMPLE 2

In Vitro Stem Cell Proliferation Inhibition Assay

Using the following test system (Lord et al., in *The Inhibitors of Hematopoiesis* pp. 227–239, 1987) the direct effect of INPROL was shown. The multilineage factor (IL-3) dependent stem cell line, FDCP mix A4 (A4), was maintained in IMDM medium supplemented with 20% horse serum and 10% WEHI-3-conditioned medium as a source of colony-stimulating IL-3.

A tritiated Thymidine incorporation assay was used to measure proliferation: A4 cells (5×10$^4$ in 100 μl medium with 20% horse serum and 50% of WEHI-3 CM) were incubated at 37° C. in 5% CO$_2$ for 16 hours.

pINPROL or the crude BME (fraction IV) were added at the start. Tritiated thymidine (($^3$H-Tdr) 3.7KBq in 50 μl at 740 GBq/mmole) was then added to each group for a further 3 hours of incubation. The level of proliferation was measured by harvesting cells and the % inhibiton calculated using the formula $$\% \text{ Inhibition} = \frac{\text{cpm without INPROL} - \text{cpm with INPROL}}{\text{cpm without INPROL}} \times (100\%)$$

Figure 6:
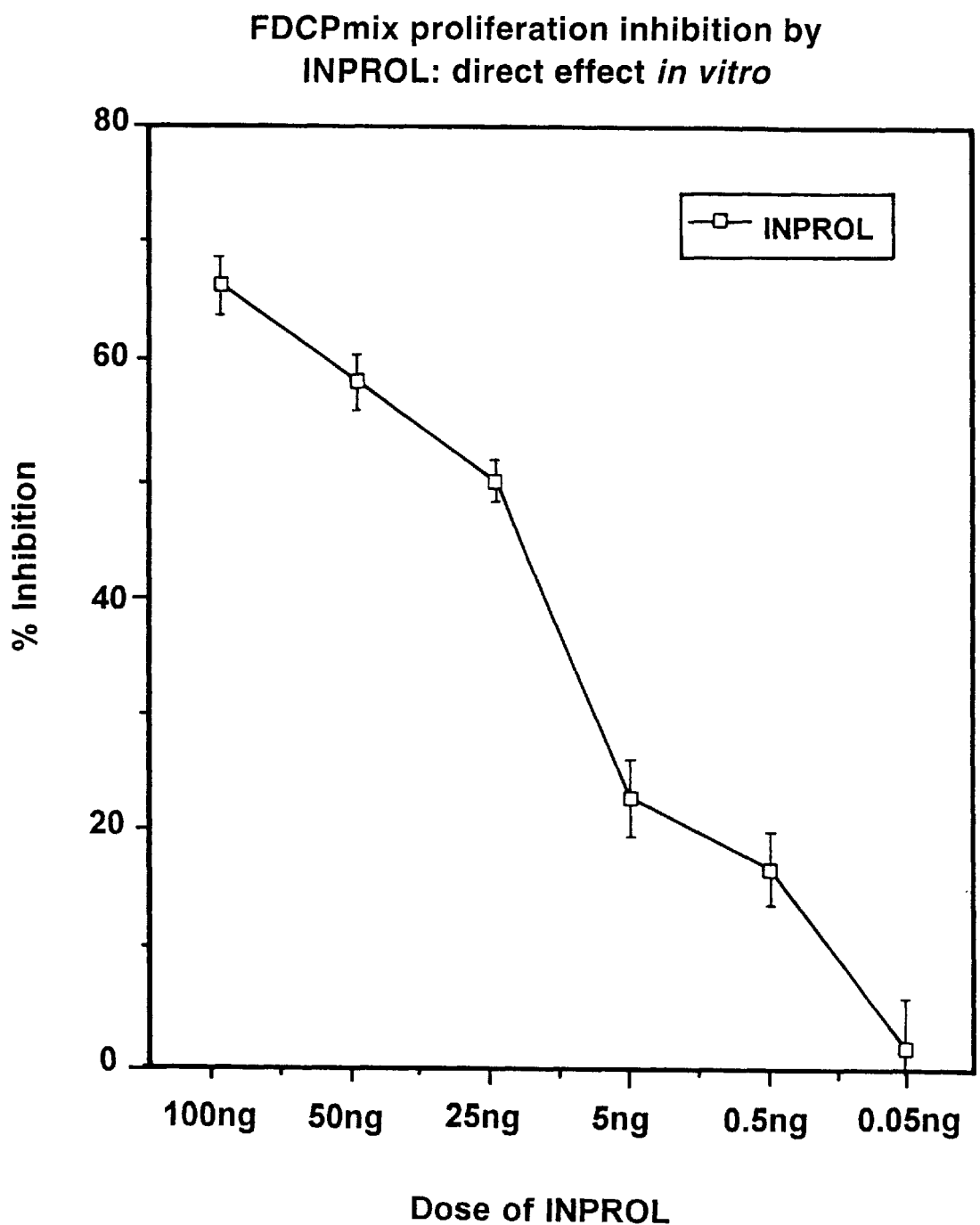
FIG. 6 shows tritiated thymidine incorporation (cpm) into cells of the FDCP-mix line without (Control=0% Inhibition) and with various concentrations of INPROL purified from porcine bone marrow (pINPROL). Data are normalized against the control value.

Incorporation of tritiated thymidine ($^3$H-Tdr) by FDCPmix-A4 cells grown in the presence of graded doses of normal bone marrow extract or pINPROL is depicted on FIG. 6. It can be seen that purified composition of pINPROL is at least 1,000 times more active than the starting material. Time of exposure (16 hours) is an important factor for effective inhibition and shows the evidence of the direct effect of pINPROL on stem cells of the A4 cell line.

EXAMPLE 3

Inhibition of CFU-S Proliferation by INPROL Injected in vivo: Doses and the Duration of the Effect The studies of the effect of INPROL injected in vivo revealed that INPROL can effectively block the recruitment of CFU-S into cycle, thus protecting those cells from the cytotoxic effect of further treatment, showing its potential for clinical use.

The experimental protocol had two goals: to check the effect of INPROL on CFU-S when injected in vivo and to define the effective duration of INPROL activity in relation to cycling stem cells.

To stimulate CFU-S proliferation, the injection of testosterone-propionate was used based on the effect mentioned above in Example 1.

Mice BDF1 were injected with TSP (10 mg/100 g) on Day 0; 24 hours later mice of each experimental group (4 mice per group) received a single pINPROL injection at doses of 0 μg, 5 μg, 10 μg, and 15 μg/mouse i.p.

Twenty-four hours after pINPROL injection, mice were sacrificed and the percent of cycling CFU-S was measured by the assay described in Example 1. TSP injection induced about 50% CFU-S into cycling in comparison with 7% in untreated mice. pINPROL in doses as low as 2 μg/mouse was able to inhibit TSP induced proliferation down to the normal level.

Figure 7:
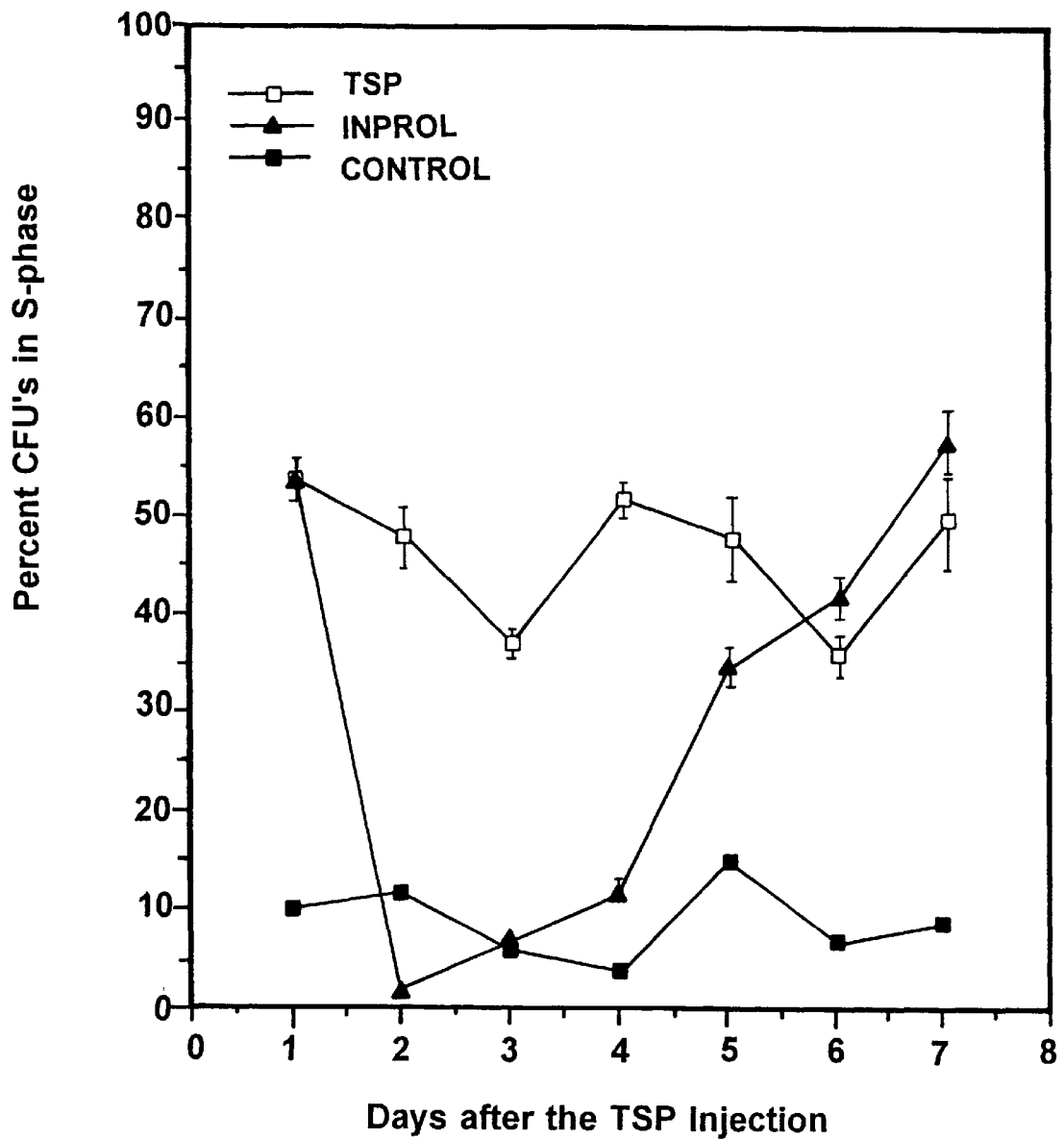
FIG. 7 shows the percent of cells in the S phase of the cell cycle after treatment of mice with testosterone propionate (TSP), TSP plus pINPROL, or vehicle (Control). Each group contained 25 animals (3–4 per time point).

For the duration of the effect evaluation, one group of mice (21 mice per group) was injected with TSP only and another group was injected both with TSP and pINPROL (24 hours after TSP). The CFU-S cycling was measured every 24 hours during a week by taking 3 donors from each group and measuring CFU-S cycle status in their bone marrow by method described (see Example 1). Data presented in FIG. 7 show that while the duration of the effect of TSP is at least 7 days, a single injection of INPROL can place CFU-S into quiescence and keep them out of cycle for no more than 48–72 hours. Since the majority of chemotherapeutic agents used for cancer and leukemia chemotherapy have a relatively short in vivo half-life, usually less than 24 hours, the INPROL effect according to the data obtained is maintained for longer than the effective time during which the chemotherapeutic agents like cytosine arabinoside or hydroxyurea are active in vivo. More importantly, for chemotherapeutic and radiation treatments having longer intervals (more than 24 hours and less than 96 hours) between the first (non-damaging for the stem cells) and the second (damaging to the CFU-S) treatments, a single injection of INPROL during the intervals between the two applications of chemotherapeutic agent or radiation should be sufficient. For several repeatable cycles of cytotoxic therapy or radiation the same strategy could be applied based on the duration of the INPROL effect.

EXAMPLE 4

Most Primitive Hematopoietic Stem Cells Stimulated to Cycle Rapidly After Treatment with 5-FU are Protected by INPROL from the Second 5-FU Exposure The drug 5-fluorouracil (5-FU) drastically reduces the number of cells in the myeloid and lymphoid compartments. It is usually thought of as being cell-cycle specific, targeting rapidly proliferating cells, because incorporation of the nucleotide analogue into DNA during S-phase of the cell cycle or before results in cell death. The long-term survival and immunohematopoietic reconstitution of the bone marrow of mice is not affected by a single dose of 5-FU; however, it was demonstrated (Harrison et al. Blood 78:1237–1240, 1991) that pluripotent hematopoietic stem cells (PHSC) become vulnerable to a second dose of 5-FU for a brief period about 3–5 days after the initial dose. It can be explained that PHSC normally cycle too slowly for a single dose of 5-FU to be effective and are stimulated into rapid cycling by stimuli resulting from the initial 5-FU treatment. We have proposed that PHSC can be returned to a slow cycle status by INPROL and thus protected from the second 5-FU treatment.

Figure 8:
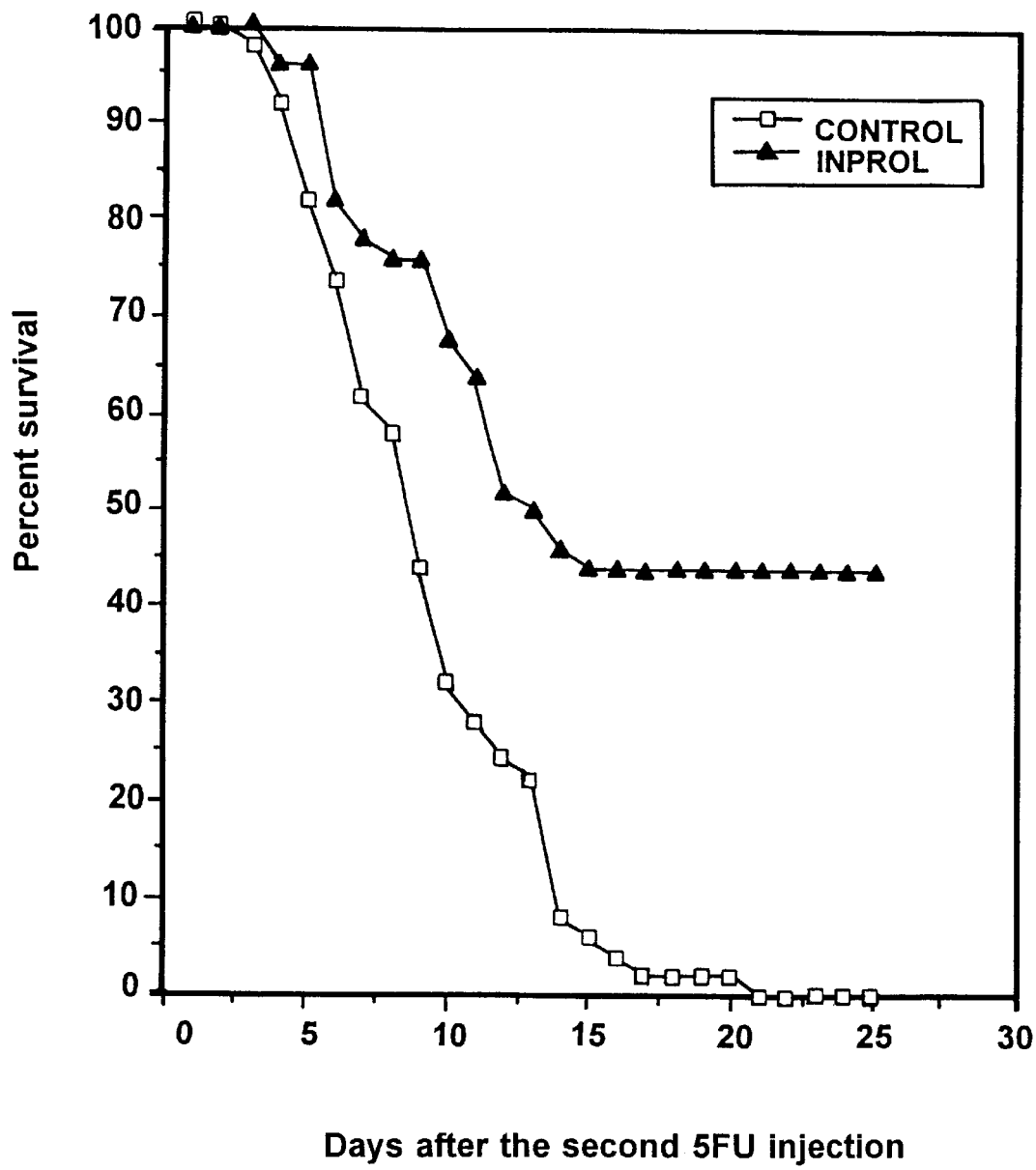
FIG. 8 shows survival of mice treated with two doses of 5-FU, with or without pINPROL treatment. Each group contained 30 animals.

The mice used in these experiments were BDF1 male mice. A stock solution of 5-FU (Sigma) was prepared in physiologic saline at a concentration of 10 $\mu$g/ml. Each treated mouse received 2 mg of 5-FU per 10 g body weight via a tail vein at Day 0 of the experiment; 24 hours later mice were injected with pINPROL (10 $\mu$g/100 g of body weight) intraperitoneally and on Day 3 were injected with the second dose of 5-FU. The survival study was conducted by monitoring the death of mice in experimental (treatment with pINPROL) and control groups of 30 mice each. The survival curves are shown in FIG. 8.

EXAMPLE 5

Effects of Pre-Incubation with INPROL vs. MIP-1α in Bone Marrow Cells

The purpose of this experiment was to compare the inhibitory effects of pre-incubation with pINPROL and MIP-1α on mouse bone marrow cells in vitro.

The following procedure was used:

in vivo: BDF1 mice, 6–15 weeks of age, are injected with 200 mg/kg 5FU i.p. 48 hours before harvesting marrow from the femurs.

in vitro: A single cell pooled suspension is counted and $5\times10^6$ cells are incubated in a total of 2 mls with or without pINPROL or MIP-1α, with 5% horse serum, IMDM media with added L-glutamine, at 37° C. and 5% $CO_2$ for 4 hours. The cells are then washed twice and recounted. They are plated in methylcellulose in the following final conditions:

0.8% methylcellulose
25% horse serum
20 ng/ml recombinant murine IL3
L-glutamine added
$5\times10^5$ cells per ml
IMDM media Plates were incubated for 11 days at 37° C. and 5% $CO_2$ in 100% humidity. Colonies more than 50 cells were counted.

TABLE 2

| Groups | Colony Number | Percent of Control |
|---|---|---|
| Control | 31.0 | 100% |
| pINPROL | 21.25 | 68.5% |
| MIP-1α | 35.25 | 114% |

EXAMPLE 6

INPROL inhibits HPP-CFC proliferation

An in vitro assay for assessing murine reconstituting stem cells and early precursors is the high proliferative potential colony (HPP-PFC) assay; other related assays, e.g., CFU-A, CFU-GM, CFU-E, and CFU-GEMM, detect progressively restricted progenitor populations (M. Moore, Blood 177:2122–2128, 1991). This example shows that pretreatment of cells with pINPROL inhibits their proliferation, whereas MIP-1α fails to do so under these experimental conditions.

BDF1 mice were treated with 5-fluorouracil (200 mg/kg i.p.) before their bone marrow was assayed for HPP-CFC numbers. Cells were washed by centrifugation and incubated at densities of $10^6$ to $5\times10^6$/ml in medium with either no added agent (Controls), pINPROL (25 ng/ml) or MIP-1α (200 ng/ml) for 4 hours. After incubation, cells were washed and plated in agar (0.3%) with 30% FCS and combined conditioned medium from 5637 and WEHI-3B cell lines (7.5% of each conditioned medium, as recommended by Sharp et al., 1991). Plating concentration was $5\times10^4$ cells/ml in 60 mm dishes. Colonies were scored on day 14 and the results are indicated below.

TABLE 3

| Group | HPP-CFU | % of Control |
|---|---|---|
| Control | 15.5 ± 1.2 | 100% |
| pINPROL | 8.3 ± 0.7 | 53.5% |
| MIP-1α | 15.8 ± 0.9 | 101% |

According to these results, MIP-1α did not inhibit proliferation of the most immature precursors when present only during the pre-incubation period. pINPROL did effectively inhibit proliferation under these conditions, indicating fundamental differences between pINPROL and MIP-1α in terms of biological activity.

EXAMPLE 7

INPROL Therapy Effect on the Recovery from Radiation-induced Bone Marrow Aplasia Bone marrow aplasia is the primary limiting toxicity of radiation cancer therapy. It has been demonstrated that some growth factors (e.g., G-CSF, GM-CSF, erythropoietin) can accelerate recovery from radiation-induced bone marrow aplasia. The concept of protection by using an inhibitor of stem cell proliferation is a different and complementary approach in coping with hematological damage. To follow the treatment procedure developed earlier (Examples 3, 4) a model of lethal irradiation of mice was established. It is known in the art that mice receiving 9Gy of cobalt 60 start dying after 10–14 days; by Day 30, mortality approximates 50%. This lethal dose was used in our model by splitting it into two subsequent applications of 4.5Gy each with an interval 3 days between doses. Preliminary data showed that the survival curve in that model was very close to that known for a single irradiation with 9Gy; moreover the test for the CFU-S proliferation showed that 24 hours after the first irradiation, 35–50% of CFU-S are induced to proliferate. Such cells can be protected by a stem cell inhibitor delivered prior to the second dose.

To examine this possibility, mice (50 mice/group) received 4.5Gy on Day 0. Twenty four hours later, one group received pINPROL (2 µg/mouse i.p.) and another, control group was injected with saline. The second dose of radiation (4.5 Gy) was given on Day 3.

Figure 9:
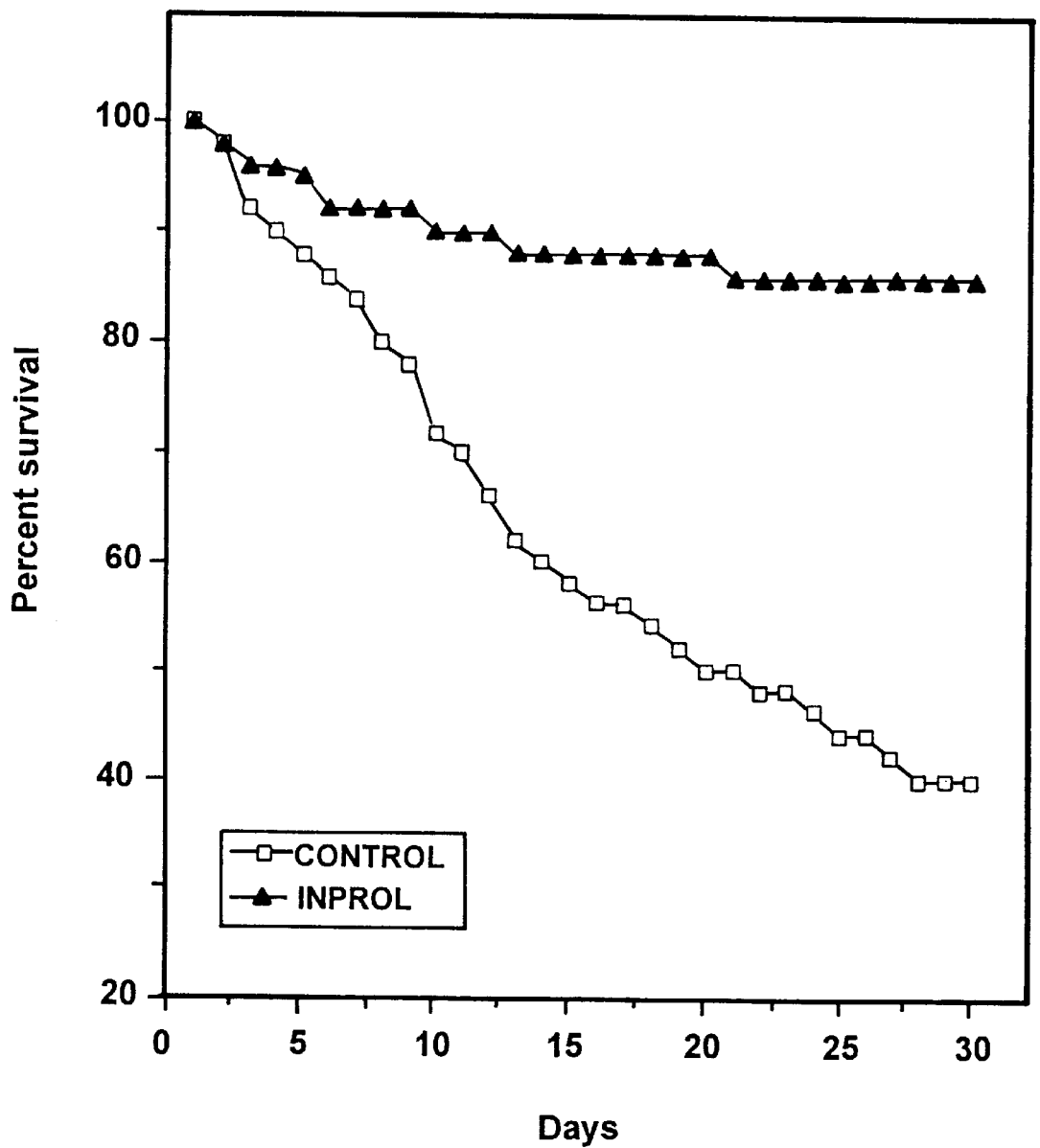
FIG. 9 shows survival of irradiated mice, with and without pINPROL treatment. Each group contained 50 animals.

FIG. 9 shows the increased survival after a single dose of pINPROL. The conditions of the model are clinically relevant for treating any cancer, including those characterized by solid tumors; such treatment would be administered to a patient having cancer by delivering an effective dose of INPROL between two consecutive dosages of radiation, thereby allowing greater dosages of radiation to be employed for treatment of the cancer. It should also be possible to extend this modality to chemotherapeutic agents.

EXAMPLE 8

INPROL Use for the Autologous Bone Marrow Transplantation

Bone marrow transplantation is the only known curative therapy for several leukemias (CML, AML, and others). Ex vivo conditioning of autologous BMT for infusion should provide potential autologous sources of normal stem cells free of leukemic contamination and able to repopulate the recipient's hematopoietic system to allow aggressive and effective therapy.

1. Long-term Bone Marrow Culture L1210 Leukemia Model For The Study Of INPROL Effect Preserving Normal Hematopoiesis During Purging With AraC Long-Term Bone Marrow Cultures (LTBMC) were established according to Toksoz et al. (Blood 55:931–936, 1980) and the leukemic cell line L1210 was adopted to the LTBMC by co-cultivation during 2 weeks. The simultaneous growth of normal and leukemic progenitors occurred in these combined LTBMC/L1210 cultures, similar to the situation in the bone marrow of a leukemic patient. Discrimination between normal colony forming units CFU and leukemic CFU was possible by growing them as agar colonies in the presence or absence of the conditioned medium from WEHI-3 (a murine IL-3 producing cell line). Normal cells undergo apoptosis in the absence of IL-3 whereas leukemic cells can form colonies in its absence. Suspension cells from LTBMC-L1210 composition give approximately 150 colonies in presence of IL-3 (normal hematopoietic clones) and 70 colonies when growing without IL-3 (leukemic clones) per 50,000 cells plated.

The procedure of purging was as follows: on Day 0 all suspension cells and media (10 ml/flask) were taken off the flasks with LTBMC-L1210 and replace with 2 ml of media containing 200 µg cytosine arabinoside (AraC) (Tsyrlova et al. in *Leukemia: Advances in Biology and Therapy* v. 35, 1988); after 20 hours of incubation, flasks were washed out and replaced with 2 ml of fresh media alone (control group) or media containing pINPROL at 25 ng/ml for 4 hours. After this preincubation, cells were incubated again with 100 µg/flask AraC for 3 hours at 37° C. Each group contained 4 flasks. LTBMC-L1210 cultures were washed 3 times and replaced with fresh LTBC media; they were maintained as before for the regeneration studies for 3–4 weeks.

Figure 10A:
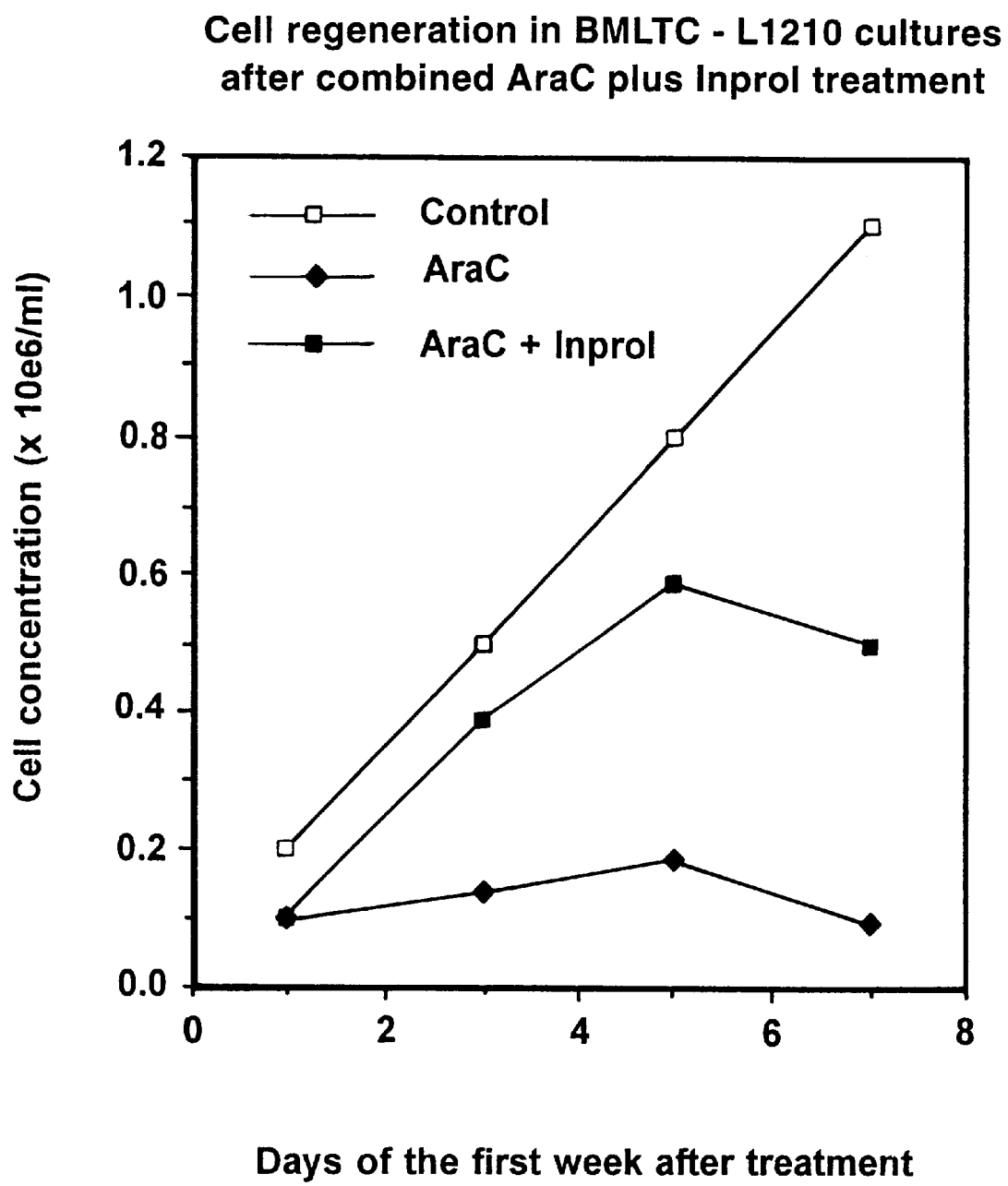
FIGS. 10A and 10B show regeneration of normal bone marrow long term culture cells 1 week (10A) and 3 weeks (10B) after treatment with Ara-C or Ara-C plus pINPROL.
Figure 10B:
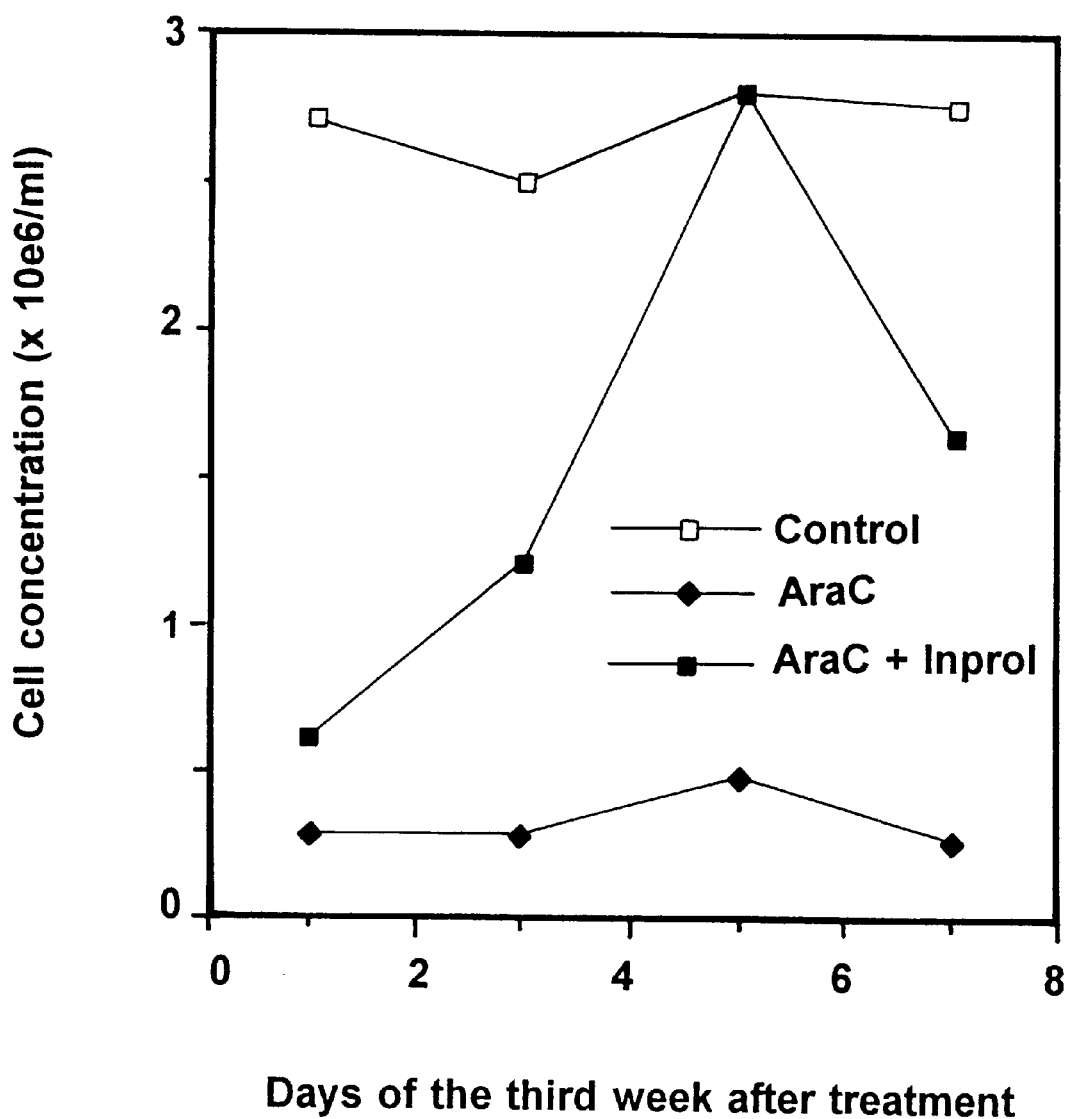

Data are presented in FIG. 10. There was no cell growth seen in control cultures treated with AraC only, while in INPROL protected flasks regeneration of hematopoiesis occurred much more rapidly due to proliferation of progenitors from the adherent layer. Moreover, the cells from the experimental group when plated in agar grew only in the presence of IL-3 giving about 100 CFU per 50,000 cells; no leukemic cell growth was observed at least during 4 weeks. Thus, marrow treated ex vivo with an effective dose of AraC in combination with INPROL can be purged of cancerous cells while the stem cells are be protected. It should be possible to extend this modality to other forms of chemotherapy or radiation treatments.

2. Marrow Repopulating Ability (MRA) And Thirty Days Radioprotection Are Increased By INPROL Treatment In Vitro MRA, the ability of cells to repopulate the bone marrow of lethally irradiated mice, together with the ability to confer radioprotection for 30 days, is a direct in vivo measurement of the potential to rescue myelosuppressed animals (Visser et al. Blood Cells 14:369–384, 1988).

Figure 11:
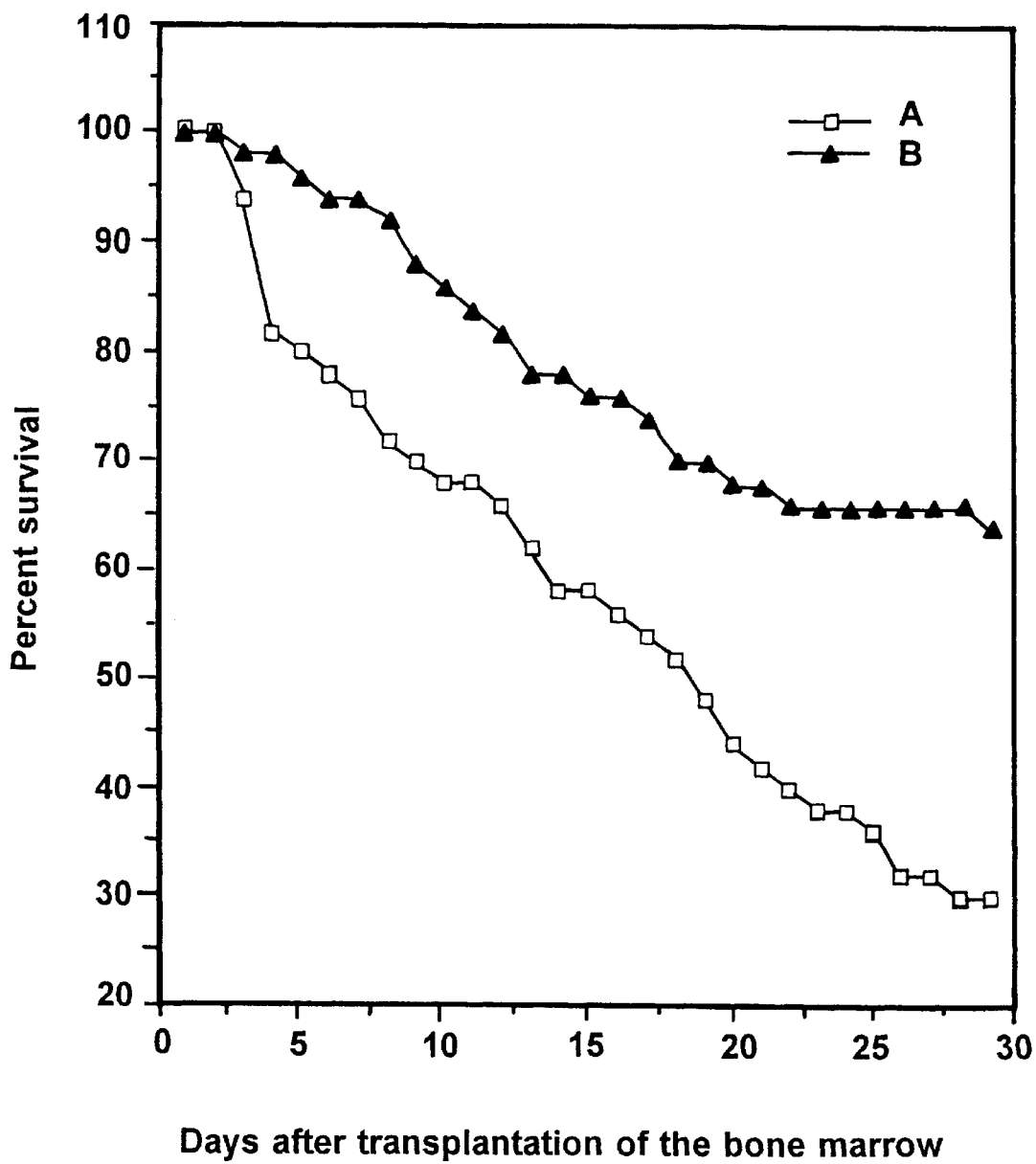
FIG. 11 shows survival of mice (75 per group) after lethal irradiation and transplantation of $3 \times 10^4$ bone marrow cells after pre-incubation with medium (Control) or pINPROL (25 ng/ml) for 4 hours. Survival was monitored for 30 days.

For radioprotection studies BDF1 mice were irradiated with 9.5Gy and restored by transplantation of bone marrow from testosterone-stimulated donors. One group of recipients was restored by bone marrow cells preincubated for 4 hours with medium (controls—group A) and another (group B) with 25 ng/ml pINPROL. Cells in both groups were washed and 30,000 cells per mouse were transplanted into irradiated animals. The survival data are shown (FIG. 11 ). The sum of 3 experiments is depicted, with controls normalized to 100%. pINPROL incubation increased the survival of mice from 36.5% in control group up to 61.8% by Day 30.

The increase of MRA induced by preincubation with INPROL could be one of the mechanisms in the improving of the radioprotection. To examine this hypothesis, MRA was measured according to Visser et al. (op. cit.). Briefly, the donor BDF1 mice were pretreated with testosterone, their bone marrow was preincubated with medium or pINPROL for 4 hours and injected into irradiated animals. On Day 13, the bone marrow cells from recipient femurs were plated in agar in 3 different concentration (0.01, 0.05, 0.1 equivalent of a femur) in the presence of 20% of horse serum and 10% of WEHI-CM. The number of Day 7 colonies represented the MRA as far as the colony-forming cells in the bone marrow of recipients at the time were the progenitors of the donor's immature stem cells.

Figure 12:
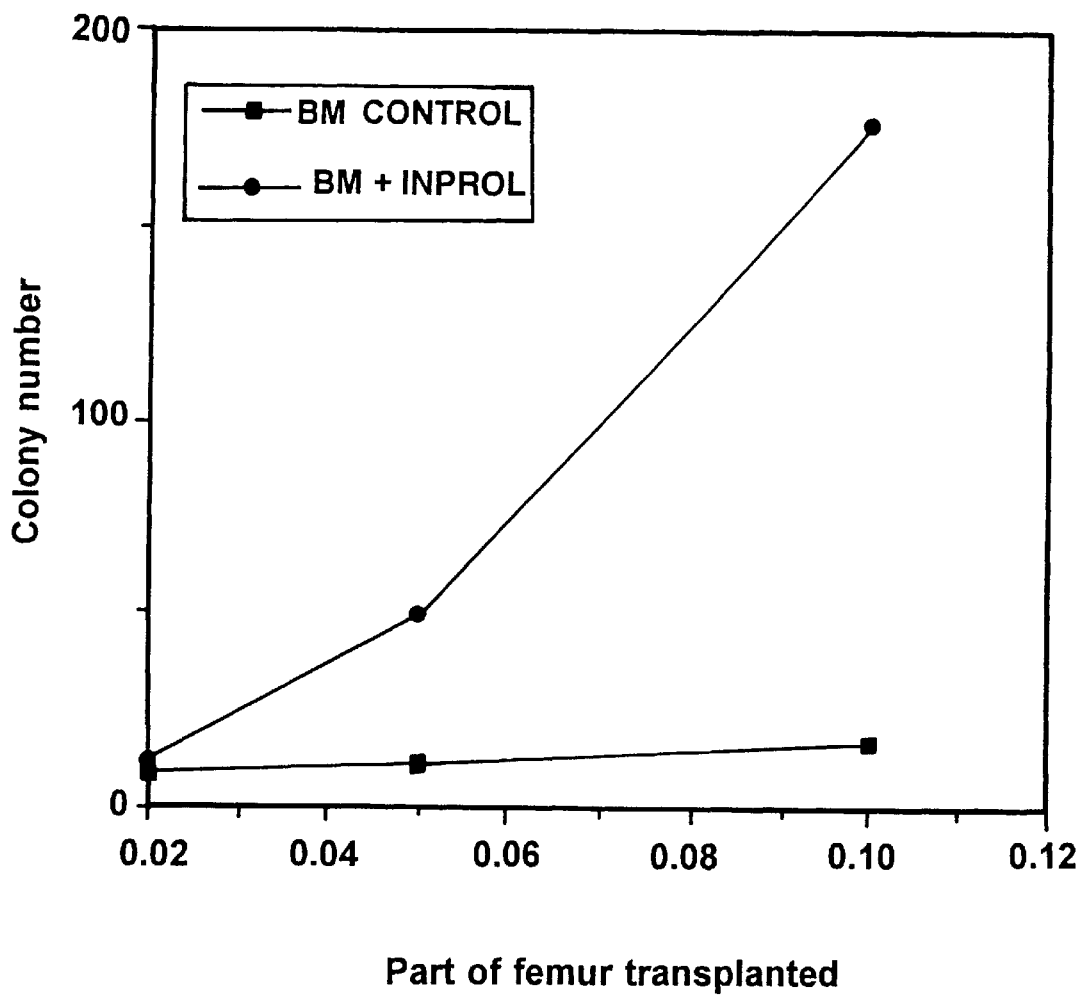
FIG. 12 shows the CFU-GM number formed after 14 days in culture by bone marrow cells from mice after lethal irradiation and restoration with donor bone marrow cells preincubated with pINPROL or medium for 4 hours.

As can be seen on FIG. 12 the MRA of the preincubated with INPROL cell population is greater than in the control group (B).

EXAMPLE 9

Antihyperproliferative Effect Of INPROL On Stem Cells Can Change Their Differentiation Abnormalities Hyperproliferation of CFU-S is not only seen during restoration from cytotoxic drugs or irradiation but also as a consequence of normal aging, and is thought to be a major feature in Myelodysplastic Syndrome (MDS). It is accompanied by the differentiation disturbances such as a prevalence of the erythroid differentiation while the differentiation along the granulocytic pathway is reduced.

Bone marrow cells were incubated for 4 hours at 37° C. with 25 ng/ml of pINPROL or media (Control), washed and then plated in agar with 20% of horse serum, 2U/ml Erythropoietin, and 10% WEHI-CM. The number of BFU-E and GM-CFU colonies were scored on Day 7. Data presented in Table 4 are summarized from 3 experiments—4 animals per point were taken for each group; 4 dishes were plated.

As is obvious from Table 4, the incubation of normal bone marrow (NBM) from intact young animals (BDF1 8–12 weeks old) with INPROL did not change the number or proportion of different types of colonies. $BDF_1$ donors pretreated with Testosterone Propionate (TSP) showed the same increase in CFU-S proliferation as was seen before (Example 1, 3, 4) a slight increase in the erythroid progenitor number (BFU-E colonies) and a decrease in GM-CFU, which were completely abrogated by the incubation with INPROL. In addition, the abnormally high level of CFU-S proliferation was returned to 10% of CFU-S in S-phase of cell cycle. CFU-S hyperproliferation is known to be a feature of some mouse strains susceptible to viral leukemia induction, for example Balb/c mice (Table 4), and can also be observed in older animals (Table 4). The same redistribution of committed progenitors seen in TSP treated BDF1 mice is observed in Balb/c and in older (23–25 month old) BDF1, which have in common the abnormally high level of CFU-S proliferation. The correction of both the proliferation of CFU-S and the differentiation was induced by the incubation with INPROL. What is even more clinically relevant, the study showed that the in vivo injection of INPROL (2 μg/mouse) affected both proliferation of CFU-S and the ratio of erythroid (BFU-E) and GM-colonies (Table 4).

TABLE 4

INPROL Effect On CFU-S Differentiation
Into Committed Progenitors BFU-E and CFU-GM

| Donors Of Bone Marrow | pINPROL | Percent CFU-S Killed by $^3$HTdR | BFU-E | CFU-GM |
|---|---|---|---|---|
| $BDF_1$ Young | − | 12.0 ± 0.3 | 28.33 ± 1.91 | 46.22 ± 3.44 |
|  | + | 15.0 ± 1.3 | 22.00 ± 3.74 | 47.70 ± 3.72 |
| $BDF_1$ Old | − | 47.1 ± 1.9 | 43.75 ± 1.54 | 24.0 ± 1.33 |
|  | + | 11.4 ± 0.7 | 15.25 ± 1.45 | 44.0 ± 7.63 |
| $BDF_1$ Stimulated by TSP | − | 53.2 ± 1.6 | 32.67 ± 2.44 | 15.71 ± 2.28 |
|  | + | 7.2 ± 0.4 | 12.00 ± 1.83 | 35.50 ± 1.4 |
| Balb/C | − | 57.0 ± 1.9 | 47.60 ± 2.96 | 33.57 ± 3.45 |
|  | + | 23.0 ± 2.4 | 24.86 ± 2.53 | 70.60 ± 4.96 |

EXAMPLE 10

Immunostimulatory Activity of INPROL

It has been observed that the incubation of bone marrow cells containing a high proportion of proliferating CFU-S with INPROL not only changes the cycling of CFU-S, but also their differentiation, switching the predominantly erythroid differentiation in favor of granulocytic and lymphoid progenitors. This property of INPROL is of importance due to the immunosuppression side effects of cytotoxic chemotherapy or radiotherapy, as well as the immunosuppression accompanying hyperproliferative stem cell disorders and aging.

The example shows the direct effect of INPROL on the differentiation of immature precursors from the Lymphoid Long Term Culture (LLTC) established according to Wittlock & Witte (Ann. Rev. Immun. 3:213–35, 1985) into pre-B progenitors, measured by the formation of colonies in methylcellulose containing IL-7.

Figure 13:
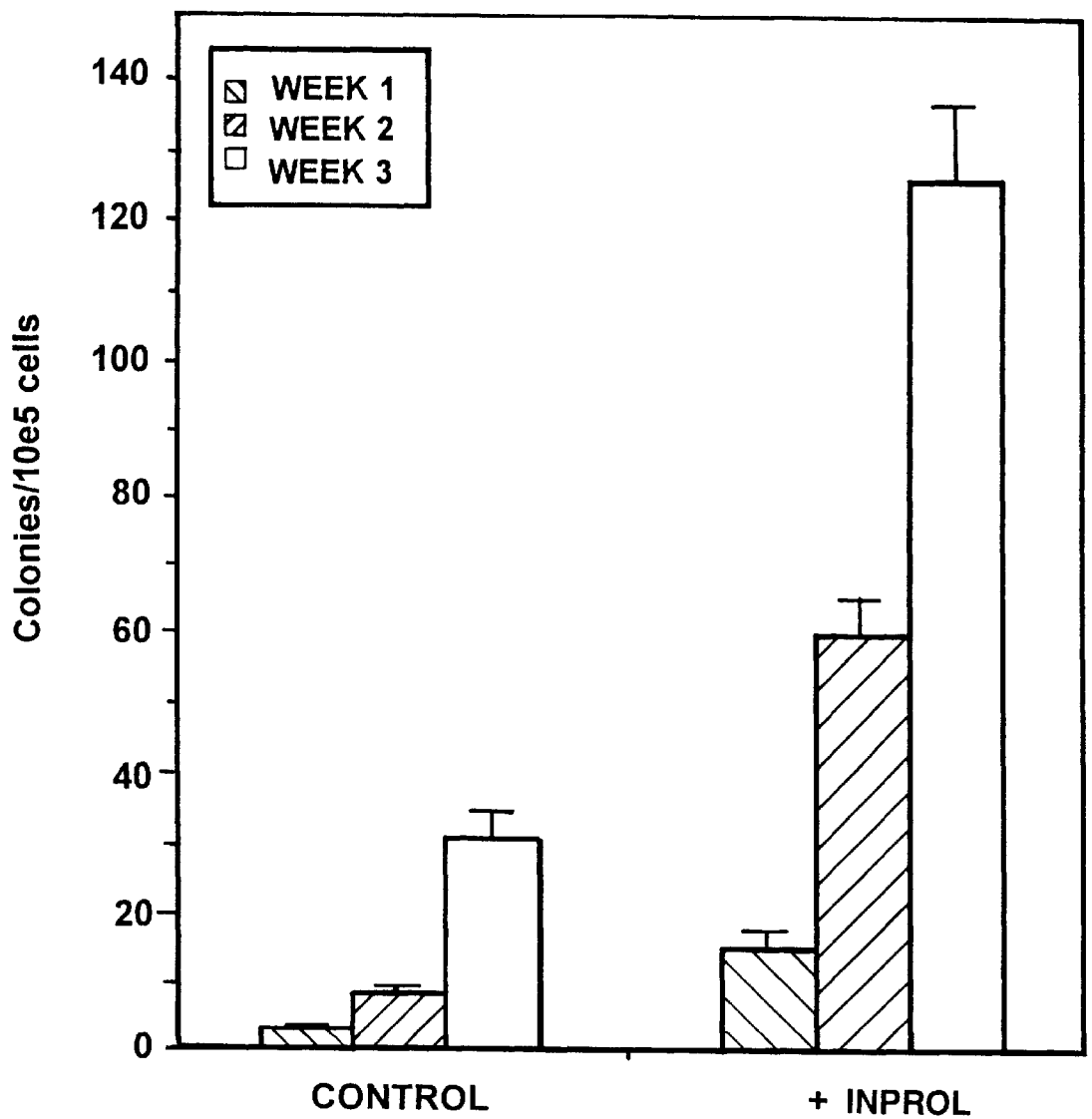
FIG. 13 shows suspension cells from lymphoid long-term culture which were taken every week, washed out, and plated with IL-7 (10 ng/ml) after preincubation with medium or pINPROL for 4 hours.

LLTC were established as described and fed with fresh LLTC-media (Terry Fox Labs., Vancouver, Canada) twice a week. Nonadherent cells were harvested once a week, washed free of factors and incubated for 4 hours with 25 ng/ml pINPROL or medium alone for control. After the incubation, the cells were washed and plated at a concentration of $10^5$ cells/ml in methylcellulose, containing 30% FCS, and 10 ng/ml of IL-7. Data from 3 weeks are shown in FIG. 13. The number of large pre-B colonies varied in control, increasing with time, but preincubation with INPROL always stimulated the growth of colonies 4 to 8 fold above the control level. This demonstrates an immunostimulatory property of INPROL which is of use in correcting immunodeficient states and in increasing desired immune responses, e.g., to vaccination.

EXAMPLE 11

INPROL Improves Repopulating Ability of Stem Cells—Long Term Culture Initiating Cells from Patient with CML Chronic myeloid leukemia (CML) is a lethal malignant disorder of the hematopoietic stem cell. Treatment of CML in the chronic phase with single-agent chemotherapy, combination chemotherapy, splenectomy, or splenic irradiation may control clinical signs and symptoms, but does not significantly prolong survival. As CML progresses from the chronic to the accelerated stage, standard therapy is not effective. At present, bone marrow transplantation (BMT) is the only known curative therapy for CML. Therapy with unrelated donor BMT is difficult due to histoincompatibility problems. Fewer than 40% of otherwise eligible CML patients will have a suitably matched related donor; therefore autologous transplantation is preferred. Ex vivo conditioning of autologous BMT for infusion together with the ability to select non-leukemic (Ph-negative) myeloid progenitors from Ph-positive patients growing in Long Term Culture (LTC) suggest the potential of autologous sources of normal stem cells to allow aggressive and effective therapy of CML.

In the context of BMT, a hematopoietic stem cell may be defined as one having the ability to generate mature blood cells for extensive periods. We have used the human LTC system developed by C. Eaves & A. Eaves both for quantitating stem cell numbers and as a means to manipulate them for therapeutic use. This involves seeding cells onto a pre-established, irradiated human marrow adherent layer; these cultures are then maintained for 5 weeks. The end point is the total clonogenic cell content (adherent+nonadherent) of the cultures harvested at the end of this time. Clonogenic cell output under these conditions is linearly related to the number of progenitors (Long Term Culture Initiating Cells (LTC-IC)) initially added; the average output from individual human LTC-IC is 4 clonogenic progenitors per LTC-IC. It has been shown previously that when marrow from patients with CML is placed under similar conditions, leukemic (Ph-positive) clonogenic cells rapidly decline. By using quantitation of residual normal LTC-IC, in patients with CML it is possible to select those likely to benefit from intensive therapy supported by transplantation of cultured autografts (Phillips et at., Bone Marrow Transplantation 8:477–487, 1991).

The following procedure was used to examine the effect of INPROL on the number of clonogenic cells (LTC-IC) among bone marrow transplant cells established from the peripheral blood of a patient with CML.

Cultures were initiated as long term cultures on preirradiated stroma. The peripheral blood of a healthy donor was used as the control. Peripheral blood cells from a CML patient were preincubated with or without pINPROL (25 ng/ml) for 4 hours, washed and placed in the LTC-IC system for 5 weeks to determine the control number of LTC-IC. For experiments, other, parallel cultures were established for 10 days. The mixture of adherent and non-adherent cells from cultures growing for 10 days was preincubated with or without pINPROL and placed on pre-established feeders for an additional 8 weeks. The number of LTC-IC from each experimental culture was estimated by plating both the adherent and non-adherent cells in methylcellulose with the appropriate growth factors (Terry Fox Laboratories, Vancouver, Canada) and counting the resulting total number of colony forming cells. The LTC-IC values obtained using this procedure were derived from assessment of the total clonogenic cells (CFC) content using the formula:

$LTC$-IIC=#CFC/4

Figure 14:
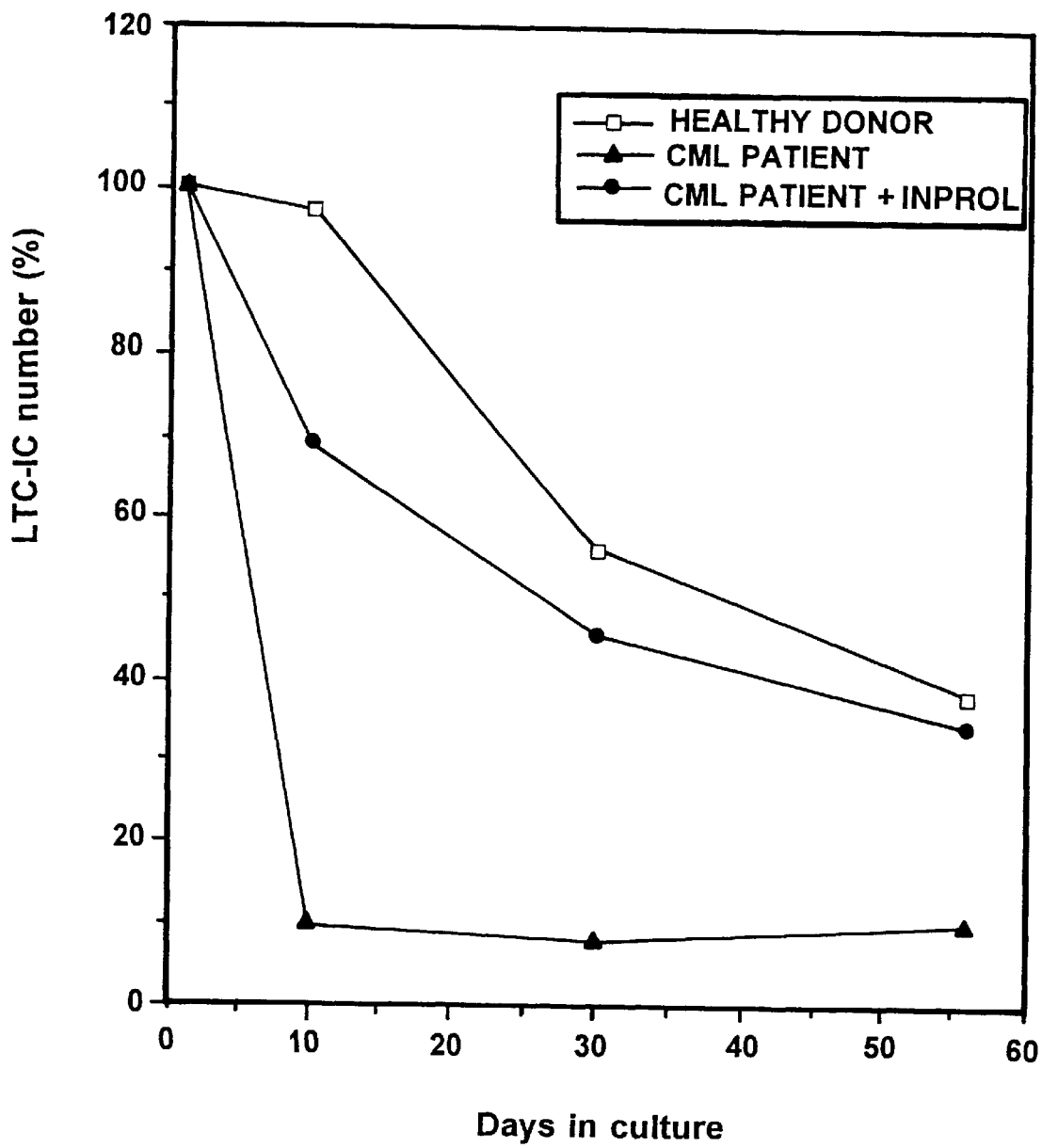
FIG. 14 shows improved repopulating ability of leukemic peripheral blood cells treated with pINPROL. Long term culture initiating cells (LTC-IC) were measured by plating adherent and nonadherent LTC cells with and without pINPROL, and scoring CFU-GM on day 7. Data are normalized to control values.

Data presented on FIG. 14 show that there was no loss in LTC-IC during the first 10 days of culture initiated from the healthy donor's bone marrow and approximately 30% of the number of input LTC-IC were still present after 5 weeks in culture. The number of the CML patient's LTC-IC was drastically reduced to about 8% during the 10 day period and did not recover during further incubation, while the preincubation of cells with INPROL increased the LTC-IC level to 30% of initial number and it was maintained during 8 weeks.

Clinically relevant applications of INPROL predicted by these preliminary data include their use in strategies for selectively improving the normal stem cell content of fresh or cultured marrow transplants, strategies for enhancing the recruitment of residual normal stem cells in vivo also protocols for transferring new genetic material into human marrow stem cells for the further transplantation into patients.

EXAMPLE 12A

A Method of Isolation of Immunoactive Inhibitor of Proliferation of Stem Cells From Bone Marrow Preparations The bone marrow was isolated from pigs' ribs. The ribs from the pigs' carcasses were separated and cleaned from the muscle fibers and fat, cut into pieces and the bone marrow was extracted by a hydropress manufactured by the Biophyzpribor. The bone marrow cells are separated by centrifugation in a centrifuge K-70 at 2,000 rpm for 20 minutes. The extract supernatant is then successively subjected to ultrafiltration through Amicon USA membranes XM-100, PM30, PM-50. According to the analysis by electrophoresis, the main component of the product is albumin (see FIG. 1).

Biochemical Purification

The bone marrow extract and protein components of the fractions were analyzed at every step of purification by gel electrophoresis in 10% polyacrylamide, containing 0.1% sodium dodecyl sulfate. Up to 7% of sodium dodecyl sulfate and up to 0.5–1% of mercaptoethanol were added to the samples which were incubated for 5 minutes at 70° C. prior to loading on the gel.

The electrophoresis was conducted at 20Y cm of the gel for five hours. Then the gel was stained in 0.25% Coomassie CBBC250 in a mixture of ethanol:water:acetic acid 5:5:1 for one hour at 20° C. and washed in several changes of 7% acetic acid. The activity of the product was evaluated by the method of inhibition of proliferation of stem hematopoietic cells (CFU-S). The method is detailed hereafter.

Stage 1. Purification by precipitation with ammonium sulfate

The activity was purified by precipitation with ammonium sulfate at 25% with saturation of 40 to 80% which was selected based on the results in Table 5.

TABLE 5

| Satuturation (%) | 0–40 | 40–60 | 60–80 | 80–100 |
|---|---|---|---|---|
| Activity (%) | 37.2–35.4 =1.8% | 37.2–1.8 =35.4% | 37.2–12.8 =24.4% | 37.2–26.1 =11.1% |

The amount of the preparation used for testing after each step of purification was determined in accordance with the level of purification and equivalent to the dose of $2\times10^{-2}$ mg of the initial product. Activity was determined by the formula:

% Change=%Sa–%Sb where

%Sa is %S in control

%Sb is %S after incubation with the test fraction.

The fraction was desalted in order to lower the concentration of ammonium sulfate 20 times before each testing of activity and before each following purification step.

Stage 2. The impure inhibitor from Stage 1 is applied after desalting and fractionated utilizing ion exchange chromatography, here DEAE 23 cellulose, and then eluted with a gradient of sodium acetate buffer (pH 6.0).

Figure 2:
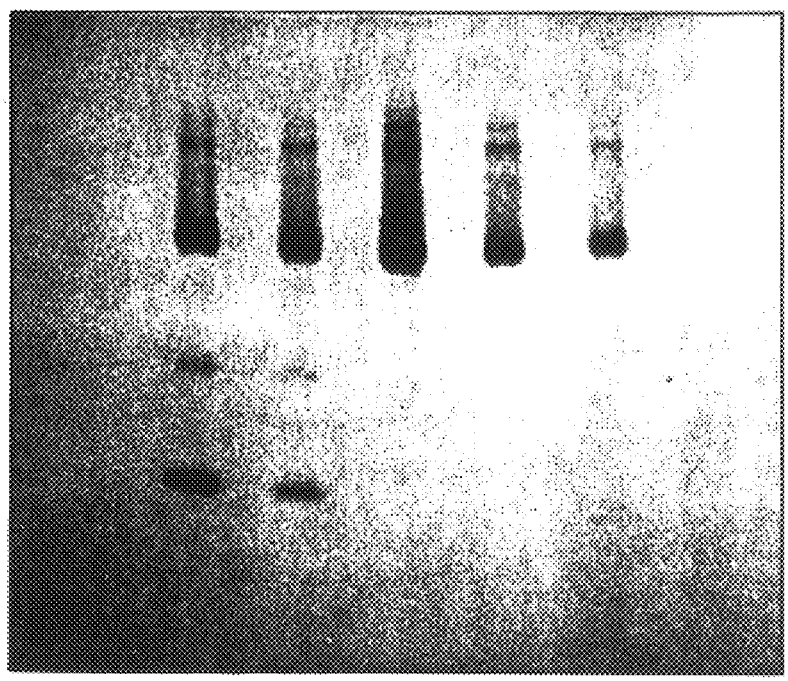

The active fractions of inhibitor elute between 3–5 mM. The volume of the column was 1 ml and speed of elution was 4 ml/hour. The detection was conducted by the chromatograph Millicrome at 230 and 280 nm. Fraction 1 (see FIG. 2) which exhibited the highest activity was isolated and eluted in 5 mM sodium acetate buffer (see Table 6).

TABLE 6

| Fractions | 1 | 2 | 3 | 4 | 5 |
|---|---|---|---|---|---|
| Activity | 46.3 – 0 = 46.3% | 46.3 – 14.1 = 32.2% | 46.3 – 42.1 = 4.2% | 46.3 – 19.6 = 26.7% | 46.3 – 45.1 = 1.2% |

Figure 3:
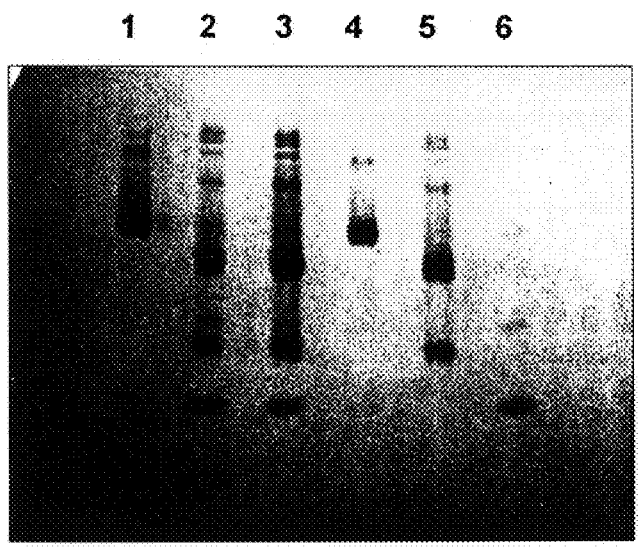

The electrophoresis data indicates that the main protein contaminant—albumin (see FIG. 3) is removed from this fraction which leads to an additional fourfold purification.

Stage 3. The partially purified inhibitor from Stage 2 is applied directly to a G-75 Sephadex column.

The volume of the column is 20 ml (20×1), the elution rate is 2 ml/hour. The elution buffer is 50 mM NaCl, 10 mM Tris-HCl, pH 7.5. Detection was conducted on a chromatograph Millichrome at 230 and 280 nm. Fraction 5 which had the highest activity was isolated.

| Time, min | % of B |
|---|---|
| 0 | 0 |
| 4 | 0 |
| 5 | 25 |
| 25 | 90 |

Stage 4. Reverse-phase chromatography (Pharmacia FPLC System) utilizing ProREC columns is performed on an Ultrasfera matrix. Protein is eluted using 0.1% trifluoracetic acid in an acetonitrile gradient.

Figure 4:
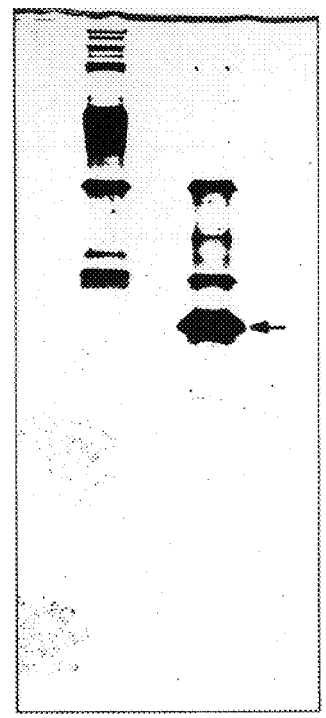

The homogeneity of a product with MW 16–17 kD is equal to 90% as was shown in analyzing the acrylamide/sodium dodecyl sulfate gel (see FIG. 6). The result is represented in FIG. 4. Activity is determined on fraction 5. The final yield of the product is 5%. As a result, the total amount of protein with MW 16 kD after the purification is 650 ng/ml of the initial product. During the purification process the product was submitted to heat incubation at 70° C. for several minutes but no loss of biological activity was detected.

EXAMPLE 12B

Alternative method for isolating larger quantities of INPROL

Initial isolation

Ribs from fresh pig carcasses are cleaned of muscle fibers and fat, then cut to pieces and soaked in phosphate-buffered saline in the ratio 1:1 (weight/volume). The obtained mixture is crushed by hydraulic press to separate bone marrow from solid bone material.

The suspension of bone marrow cells is collected and filtered free of solid particles through four layers of the cheese-cloth. The filtrate is incubated at 56° C. for 40 minutes, then cooled in an ice bath to 4° C. The resulting precipitate is removed by centrifugation at 10,000 g for 30 minutes at 4° C. and discarded.

The clarified supernatant is added dropwise during 30 minutes to 10 volumes of stirred ice-cold acetone containing 1% by volume of concentrated hydrochloric acid. The resulting mixture is kept at 4° C. for 16 hours for complete formation of the precipitate. Then the precipitate is pelleted by centrifugation at 20,000 g for 30 minutes at 4° C. This pellet is washed with cold acetone and dried.

HPLC Purification

The pellet is dissolved in HPLC eluent buffer A containing 5% acetonitrile (MeCN) and 0.1% triflouroacetic acid (TFA) to final protein concentration 8–10 mg/ml. This solution (0.5–0.6 ml) is loaded onto 250×4.6 mm HPLC column packed with Polisil ODS-300 (10 mcm) and equilibrated with the same buffer A.

The elution is accomplished by gradient of buffer B (90% MeCN, 0.1% TFA) in buffer A at the flow rate of 1 ml/min according to the following program:

| Time, min | % of B |
|---|---|
| 0 | 0 |
| 4 | 0 |
| 5 | 25 |
| 25 | 90 |

Figure 5:
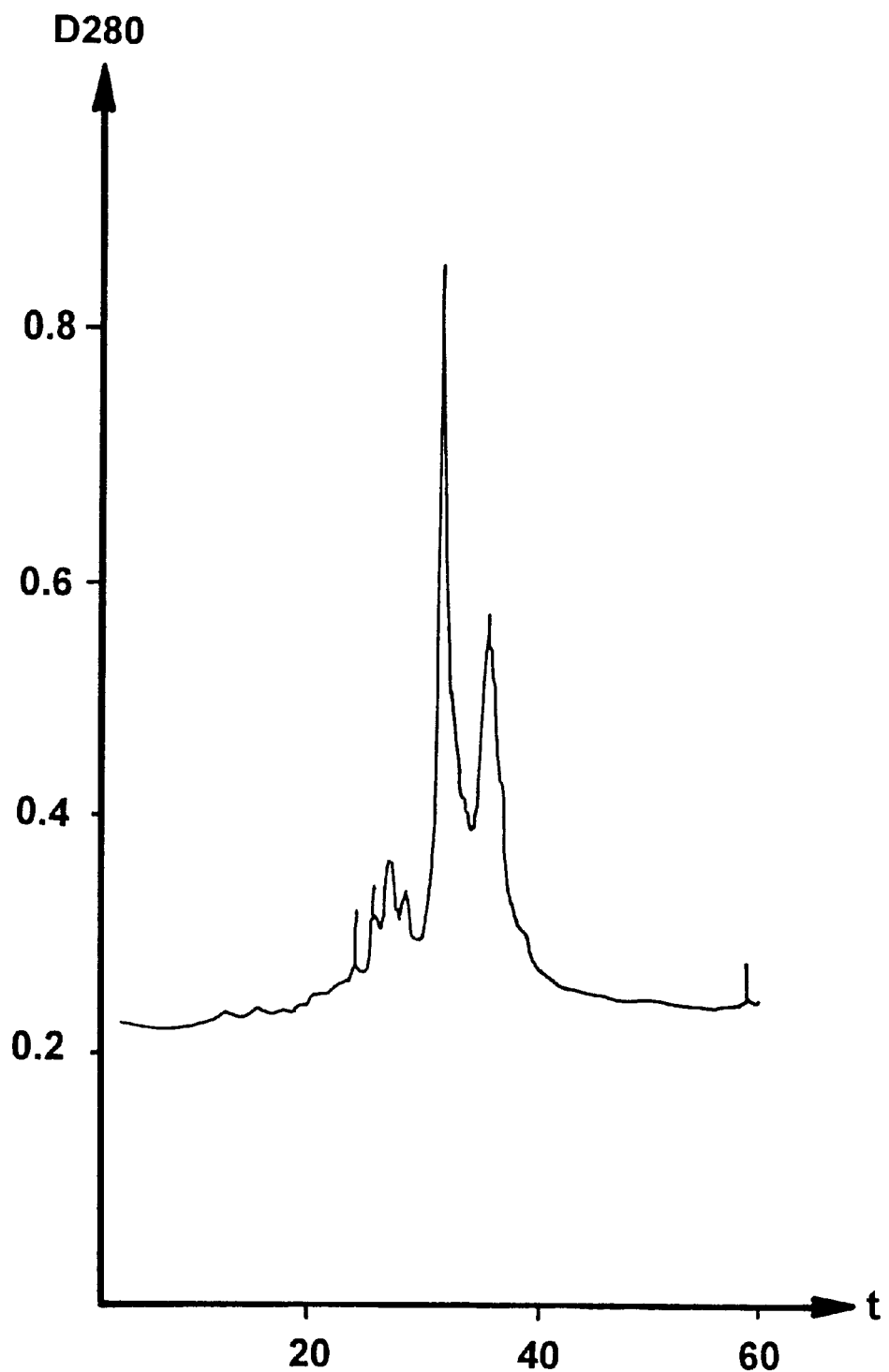
FIG. 5 shows a reverse phase HPLC chromatogram of the final purification.

An additional step of 100% B for 5 minutes is used to wash the column prior to re-equilibration. Then the column is equilibrated again for returning it to the initial state, and the next portion of the protein solution may be loaded. A typical chromatogram is shown in FIG. 5.

During the separation the column effluent is monitored at 280 nm for the detection of protein peaks. Fractions containing the protein material are collected, separated peaks are pooled and rotary evaporated at 30° C. to dryness. The obtained residues are dissolved in distilled water and assayed by bioactivity test and by SDS-PAGE (14% gel, reducing conditions). The peak containing the active material is eluted between 70 and 80% of the buffer B and contains the main protein band of 16 kD and the traces of faster moving proteins as assayed by SDS-PAGE.

Figure 15A:
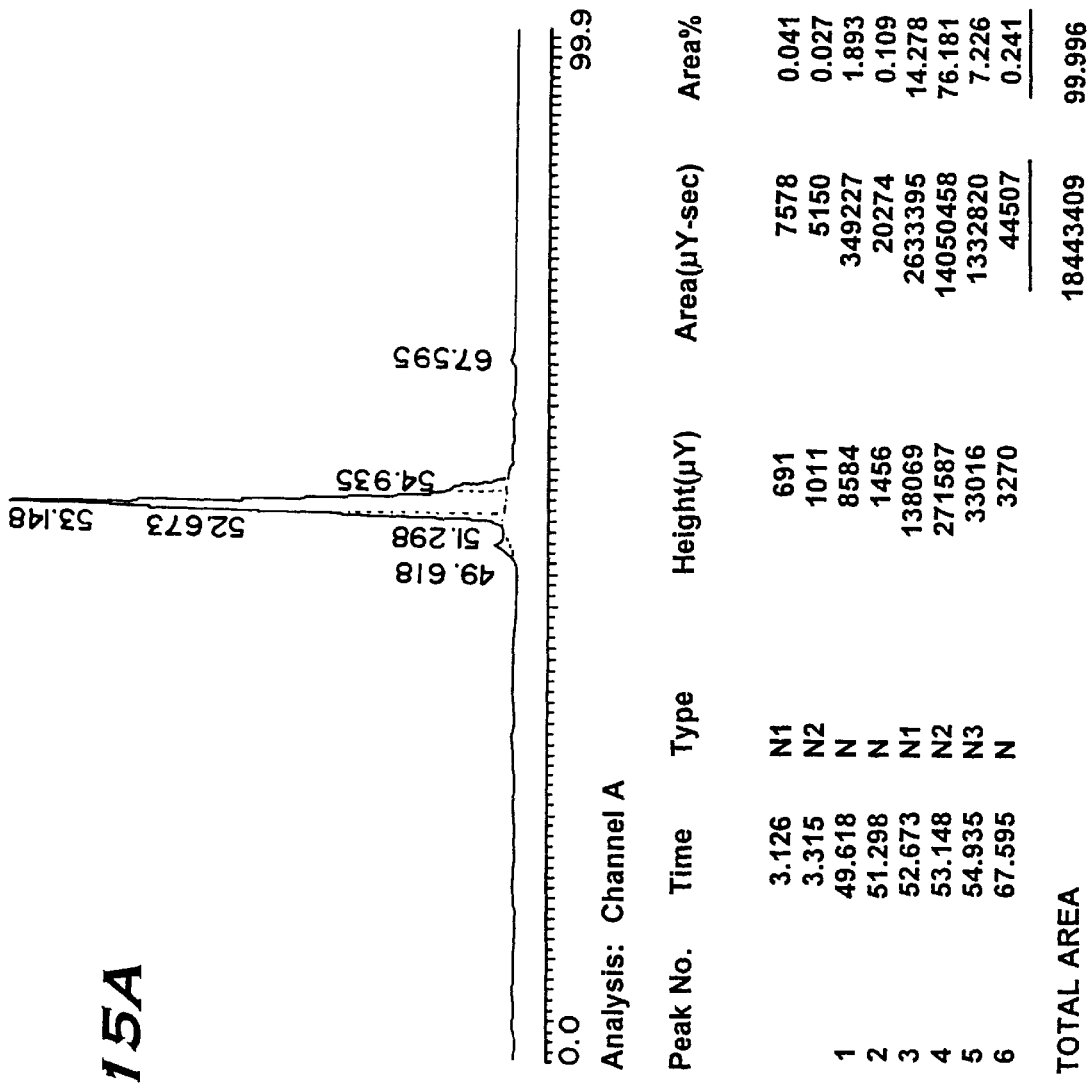
FIG. 15A shows a C4 reverse phase chromatogram of purified pINPROL eluting at 53% acetonitrile. Lane 1 is the crude material, Lane 2 is molecular weight markers and Lane 3 is the purified material.
Figure 15B:
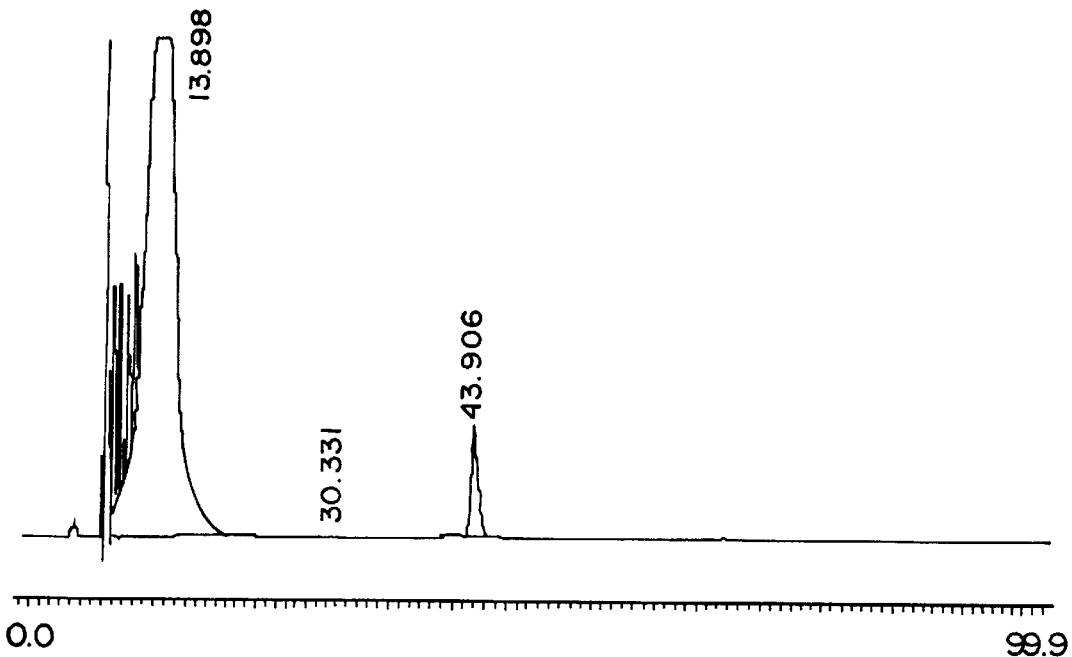
FIG. 15B shows a C4 reverse phase chromatogram of MIP-1α eluting at 43.9% acetonitrile.

An analysis of the material obtained by collecting only the second major HPLC peak is shown in FIG. 15 (A and C). Material containing both peaks (e.g., FIG. 5) will be referred to herein as pINPROL Preparation 1 and those consisting of only the second peak will be referred to as pINPROL Preparation 2. 500 ug of this active, purified pINPROL Preparation 2 was loaded onto a C4 reverse phase column (Vydac) and eluted using a linear gradient of 595% acetonitrile in 0.1% trifluoroacetic acid. The material eluted as a single peak at 53% acetonitrile (FIG. 15A). When 250 µg of MIP-1α (R&D Systems), however, was run under identical conditions, it eluted at 43.9% acetonitrile (FIG. 15B—note that earlier peaks prior to 14% acetonitrile are artifactual and due to air bubbles in the detector). Thus, naturally occuring INPROL is substantially more hydrophobic than MIP-1α under these conditions. TGFβ is known to elute at lower concentrations than that observed for pINPROL under these conditions (Miyazono et al. J. Biol. Chem. 263:6407–15, 1988).

Figure 15C:
FIG. 15C shows an SDS-PAGE chromatogram of the crude pINPROL preparation and of the purified preparation after reverse phase.

A gel of the eluted pINPROL material is shown in FIG. 15C. Lane 1 is the crude material, Lane 2 is molecular weight markers and Lane 3 is the purified material. There are two major bands, one at approximately 14 kD and one at approximately 35 kD. It is believed that the 35 kD band is a multimeric form of the 14 kD band.

EXAMPLE 13A

Active INPROL Preparations Contain Hemoglobin Beta Chain pINPROL was prepared as shown in FIG. 5 (i.e., pINPROL Preparation 1 (see Example 12B)). The material was run on SDS-PAGE and transferred to nitrocelluose using standard techniques. The material was subjected to N-terminal sequence analysis using an ABI 477A protein sequencer with 120A Online PTH-AA analyzer using standard techniques. The following N-terminal sequence was obtained:

VHLSAEEKEAVLGLWGKVNVDEV . . . (SEQ ID NO:23)

Computer search of the protein databases reveal that this sequence has identity with the N-terminal sequence of the beta chain of porcine hemoglobin (cf. FIG. 16C).

EXAMPLE 13B

Active INPROL Preparations Contain Hemoglobin Alpha Chain

As shown in FIG. 15C, protein purified by collecting the second major peak shown in FIG. 5 (i.e., pINPROL Preparation 2 ) resulted in two major bands corresponding to molecular weights of approximately 15 K and 30 K, as well as several minor bands. SDS-PAGE gels were transferred to nitrocellulose using standard techniques and individual bands were excised and subjected to N-terminal sequence analysis as in Example 13A. The following N-terminal sequence was obtained for the 15 kD band:

VLSAADKANVKAAWGKVGGQ . . . (SEQ ID NO:24)
The 30 kD band was subjected to limited proteolytic digest and the following internal sequence was obtained: **FPHFNLSHGSDQVK . . . (SEQ ID NO:25)

The first sequence shows identity with the N-terminal sequence of porcine hemoglobin alpha chain whereas the second sequence shows identity with residues 43–56 of the porcine hemoglobin alpha chain (see FIG. 16C for a sequence comparison of human, murine and porcine alpha and beta hemoglobin chains). Repeat sequencing of these bands as well as of some of the minor bands consistently yielded portions of the alpha globin sequence. Thus the various bands observed in FIG. 15C represent either fragments or aggregates of the porcine hemoglobin alpha chain.

EXAMPLE 13C

Further characterizations of Porcine INPROL

Figure 17A:
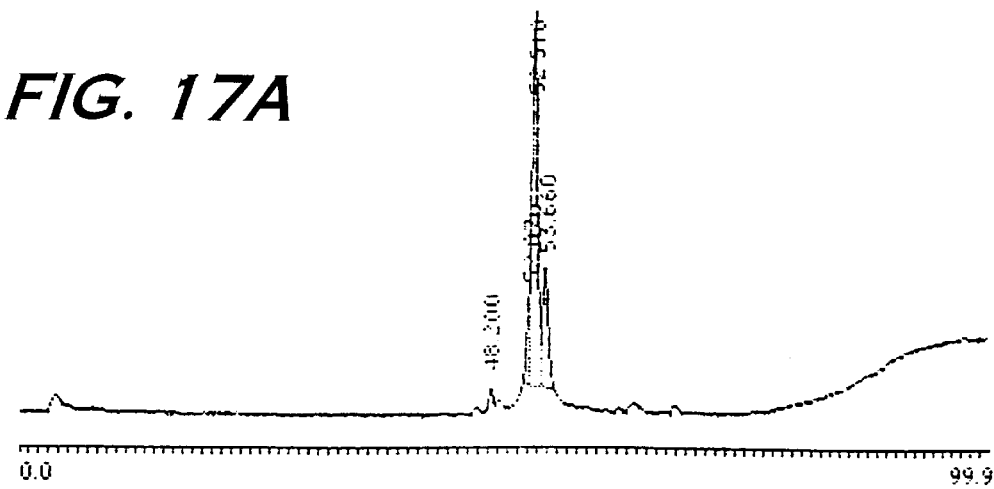
FIG. 17 shows a comparison of the $C_4$ reverse-phase HPLC traces of pINPROL (FIG. 17A) and of crystallized pig hemoglobin (FIG. 17B).
Figure 17B:
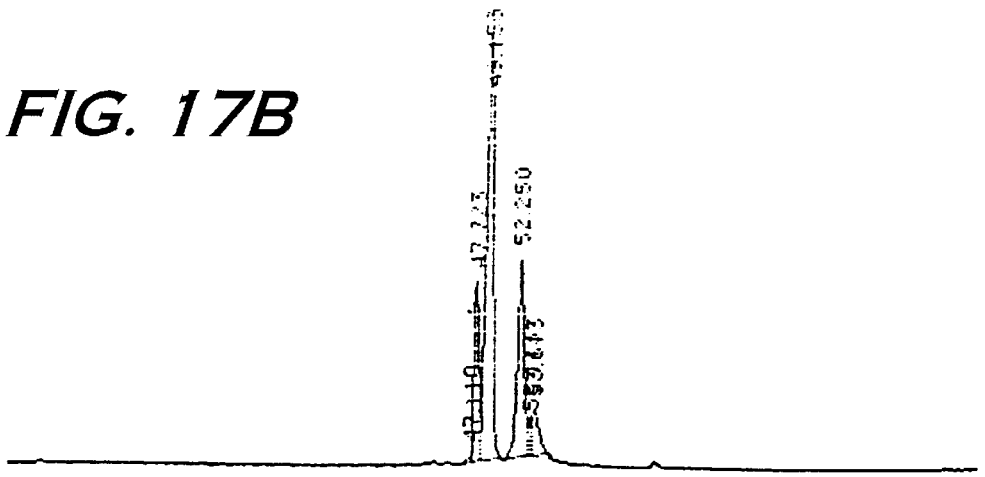

In order to further compare pINPROL to porcine hemoglobin, twice crystallized porcine hemoglobin was obtained from Sigma Chemical Company and subjected to reverse phase HPLC as described in Example 12B for FIG. 15. As can be seen in FIG. 17, the HPLC chromatogram of intact hemoglobin is similar to that seen for the pINPROL Preparation 1. Further, in a direct comparison, the pINPROL Preparation 2 shown in FIG. 17A (i.e., derived from the second peak of FIG. 5) is seen to overlap with that of the second two peaks of porcine hemoglobin (FIG. 17B), with retention times of 52.51 and 52.25 minutes for the major peaks, respectively. It should be noted that heme co-migrates with the first major peak in hemoglobin, in this case at 49.153 minutes; heme is therefore a component of pINPROL Preparation 1 but not of Preparation 2. This is confirmed by the lack of absorption of this pINPROL preparation at 575 nm, a wavelength diagnostic for the presence of heme.

Figure 18:
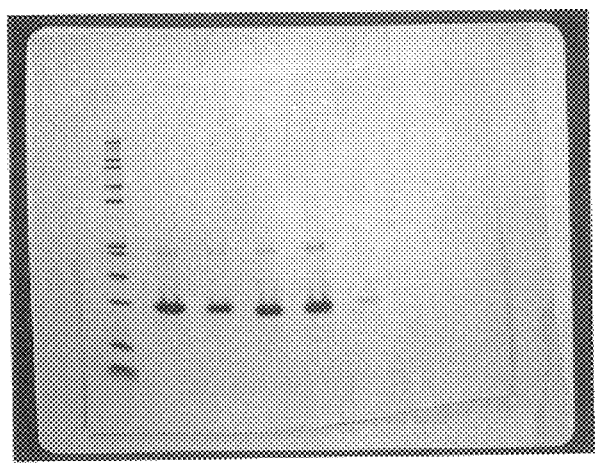
FIG. 18 shows an SDS-PAGE gel of fractions from a $C_4$ reverse phase HPLC separation of crystallized pig hemoglobin. Lane 1 shows molecular weight markers, Lane 2 shows Fractions 48–49, derived from the first peak (at 47.11 min), Lane 3 shows fractions 50–51, derived from the second peak (at 49.153 min), Lane 4 shows fractions 54–55, derived from the third peak (at 52.25 min) and Lane 5 shows fractions 56–57, derived from the fourth peak (at 53.613 minutes).

The predicted molecular weights of porcine hemoglobin alpha and beta chains are 15038 Daltons and 16034 Daltons, respectively. As can be seen in the SDS-PAGE chromatogram in FIG. 18, the first two peaks are composed of the higher molecular weight chain and the second two are composed of the lower molecular weight chain. Thus the first two peaks appeared to represent hemoglobin beta chain and the second two peaks to represent hemoglobin alpha chain.

Figure 21:
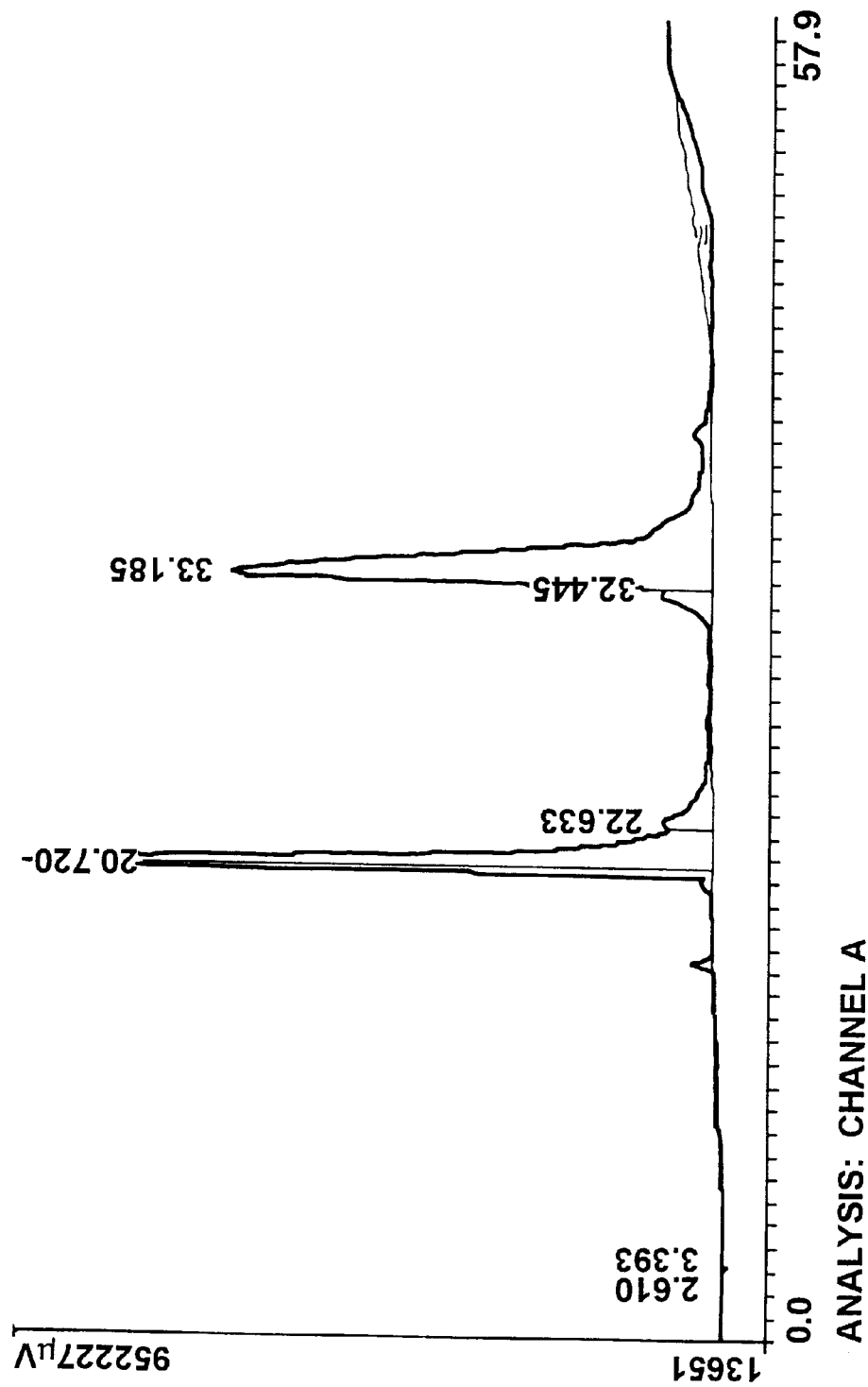
FIG. 21 shows the reverse phase separation of porcine hemoglobin using a shallow elution gradient.

Additional separations of porcine hemoglobin were carried out using a shallow elution gradient (FIG. 21). N-terminal analyses of these peaks demonstrated that the first peak is porcine alpha chain and the second porcine beta chain. Bioassay results confirm that both isolated hemoglobin chains are biologically active (e.g., Examples 14 and 15).

Figure 19A:
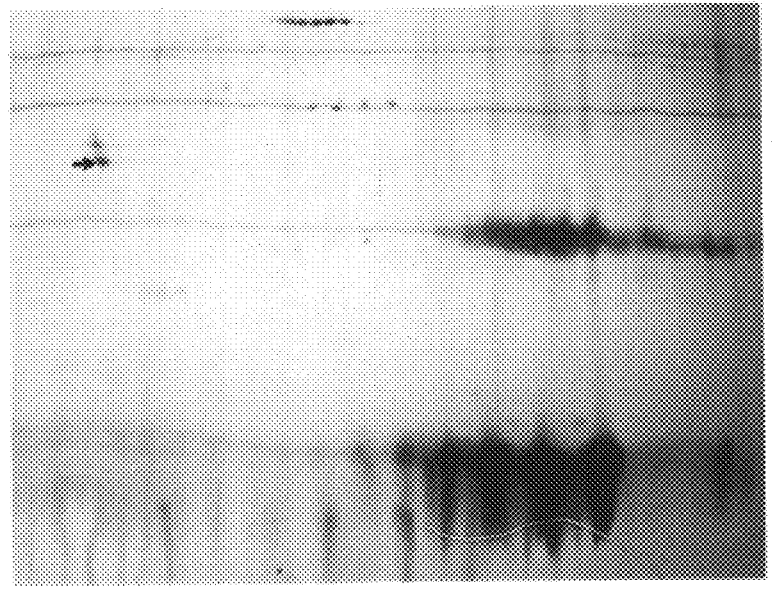
FIGS. 19A–B show a comparison of the 2-dimensional gel electrophoreses of pINPROL (FIG. 19A) and of purified pig beta hemoglobin (FIG. 19B).
Figure 19B:
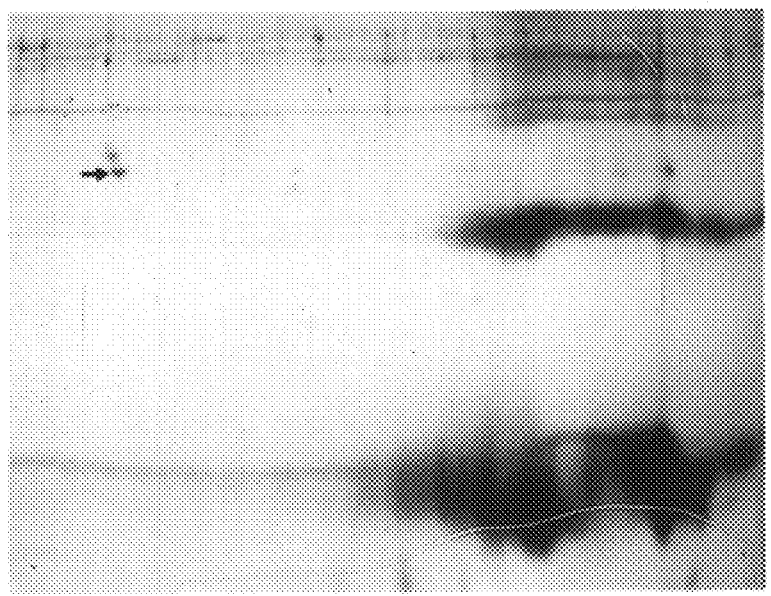

In order to further compare pINPROL Preparation 2 and hemoglobin beta chain, 2-dimensional electrophoreses were conducted (FIG. 19). As a first dimension, isoelectric focusing was carried out in glass tubes using 2% pH 4–8 ampholines for 9600 volt-hours. Tropomyosin (MW 33 kD, pI 5.2) was used as an internal standard; it's position is marked on the final 2D gel with an arrow. The tube gel was equilibrated in buffer and sealed to the top of a stacking gel on top of a 12.5% acrylamide slab gel. SDS slab gel electrophoresis was carried out for 4 hours at 12.5 mA/gel. The gels were silver stained and dried.

A comparison of the 2D electrophoretic patterns revealed only one or two minor spots that are different between HPLC purified hemoglobin beta chain and the pINPROL Preparation 2. Western analyses, using anti-porcine hemoglobin antibodies and either 1D or 2D electrophoresis, confirm the presence of beta hemoglobin in the preparation. Thus the active pINPROL Preparation 2, prepared according to Example 12B, is substantially porcine hemoglobin beta chain.

EXAMPLE 14

Hemoglobin Alpha Chain, Hemoglobin Beta Chain or Intact Hemoglobin Exhibit Stem Cell Inhibitory Activity To confirm that hemoglobin beta chain has INPROL activity, a suicide assay using bone marrow from testosterone-treated mice was conducted using the methodology described in Example 1 using material purified as in Example 12B. As shown in Table 8, 15% of normal mouse bone marrow cells were killed as opposed to 36% in the testosterone-treated animals. As expected, this indicated that testosterone treatment increases the percentage of cells in cycle (thus rendering them more susceptible to killing—e.g., Example 1). In sharp contrast, cells from testosterone-treated animals incubated with either pINPROL or purified hemoglobin beta chain at 40 ng/ml showed a dramatic lowering of the percentage of cells in cycle from 36% to 0% and to 7%, respectively. The higher dose of 200 ng was less effective for both proteins. As a positive control, the previously characterized stem cell inhibitor MIP-1α reduced cycling to 13%.

A similar assay can be performed in vitro, using the cycling status of CFU-MIX instead of CFU-S. The assay is performed as described above for the CFU-S assay except that cytosine arabinoside (Ara C, 30 mg/ml) is used as the cycle-specific toxic agent instead of high dose tritiated thymidine (see B. I. Lord in *Haemopoiesis—A Practical Approach*, N. G. Testa and G. Molineux (Eds.), IRL Press 1993; Pragnell et al. in *Culture of Hematopoietic Cells*, R. I. Freshney, I. B. Pragnell and M. G. Freshney (Eds.), Wiley Liss 1994) and a mouse strain with high endogenous cycling rates (Balb/c) is used instead of testosterone-treated $BDF_1$ mice. As shown in Table 9, highly purified porcine beta chain, or highly purified porcine alpha chain, are both active in this assay. Note that in this assay, cycling levels for cells treated with pINPROL occasionally have negative numbers, indicating that there are even more colonies in the Ara C treated pool than in the non-treated pool.

As described in Example 2, pINPROL inhibits the proliferation of the murine stem cell line FDCP-MIX in a tritiated thymidine uptake assay. FIG. 20 demonstrates that purified hemoglobin alpha or beta chains are both active in this assay, with inhibitions seen at<2ng/ml.

The foregoing provides evidence that the beta chain of porcine hemoglobin exhibits INPROL activity. Other data (e.g., Table 9, FIG. 20) demonstrate that isolated alpha chain, as well as intact hemoglobin, are also active as stem cell inhibitors. Active preparations also include mixtures of alpha and beta chains (e.g., FIG. 5).

The observations that isolated alpha globin chain and/or isolated beta globin chain are active indicate that the activities described here do not require an intact three-dimensional hemoglobin structure. Fragments of alpha and beta chain are also active as stem cell inhibitors.

TABLE 8

| Treatment | % Kill |
| --- | --- |
| NBM[1] | 15 |
| TPBM[2] | 36 |
| pINPROL 200 ng/ml | 23 |
| 40 ng/ml | 0 |
| Hbg[3] 200 ng/ml | 25 |
| 40 ng/ml | 7 |
| MIP-1α 200 ng/ml | 13 |

[1]NBM = Normal Bone Marrow
[2]TPBM = Bone marrow from testosterone-treated mice
[3]Hbg = $C_4$ Reverse-phase purified porcine hemoglobin beta chain (derived from 2X crystallized pig hemoglobin)

TABLE 9

| Treatment | % Kill |
|---|---|
| Control[1] | 43 |
| Porcine alpha chain[2] | −4 |
| Porcine beta chain[2] | −14 |

[1]Control - Bone marrow from Balb/c mice
[2]100 ng/ml (Purified as in FIG. 21)

EXAMPLE 15

Purified INPROL, Purified Porcine Alpha Hemoglobin or Purified Porcine Beta Hemoglobin are Active In Vivo In order to test the ability of purified porcine hemoglobin chains to act in vivo, $BDF_1$ mice were injected with testosterone propionate as described in Example 1. Twenty four hours later, mice received 500 ng of either pINPROL, porcine hemoglobin alpha chain (purified from peripheral red blood cells as in FIG. 21), porcine beta chain (purified from peripheral red blood cells as in FIG. 21) or the equivalent volume of carrier intravenously. Forty eight hours later the bone marrow from each mouse was harvested and the CFU-MIX assay conducted as described in Example 14. As shown in Table 10, pINPROL, pig alpha chain and pig beta chain all were active in vivo, reducing the per cent of CFU-MIX in cycle to basal levels.

TABLE 10

| Treatment | % Kill |
|---|---|
| Control[1] | 45 |
| pINPROL[2] | 5 |
| Porcine alpha chain[2] | 5 |
| Porcine beta chain[2] | −5 |
| Basal[3] | 4 |

[1]Control - Bone marrow from testosterone-treated $BDF_1$ mice
[2]100 ng/ml
[3]Basal - Bone marrow from untreated $BDF_1$ mice

EXAMPLE 16

Purified Human Hemoglobin Alpha Chain, Biotinylated Human Hemoglobin Alpha Chain, Biotinylated Human Hemoglobin Beta Chain, Human Hemoglobin Gamma Chain and Human Hemoglobin Delta Chain All Exhibit Stem Cell Inhibitory Activity In Vitro Human hemoglobin was obtained either from Sigma Chemical Corporation or was isolated by standard means from adult human peripheral blood or umbilical cord blood. Individual chains were isolated by reversed-phase HPLC in a similar manner as that described above for porcine alpha and beta chains (see B. Masala and L. Manca, Methods in Enzymology vol. 231 pp. 21–44, 1994). Purified alpha, beta, gamma and delta chains were obtained. For biotinylated alpha and beta chains, 1 mg of adult human hemoglobin was treated with 37 μg of NHS LC Biotin (Pierce) and the chains separated by reverse phase chromatography as above.

As shown in Tables 11, 12 and 13, purified human alpha, biotinylated human alpha, biotinylated human beta, human gamma and human delta hemoglobin chains are all active in the CFU-MIX cycling assay.

TABLE 11

| Treatment | % Kill |
|---|---|
| Control[1] | 49 |
| Human alpha chain[2] | −1 |
| Human beta chain[2] | 41 |
| Human gamma chain[2] | −63 |

[1]Control - Bone marrow from Balb/c mice
[2]100 ng/ml

TABLE 12

| Treatment | % Kill |
|---|---|
| Control[1] | 47 |
| Human gamma chain[2] | 12 |
| Human delta chain[2] | −4 |

[1]Control - Bone marrow from Balb/c mice
[2]100 ng/ml

TABLE 13

| Treatment | % Kill |
|---|---|
| Control[1] | 68 |
| Human alpha chain[2] | 19 |
| Biotinylated alpha chain[2] | 7 |
| Human beta chain[2] | 55 |
| Biotinylated beta chain[2] | 25 |

[1]Control - Bone marrow from Balb/c mice
[2]100 ng/ml

EXAMPLE 17

Purified Human Alpha Chain, Alpha-Beta Dimer or Hemoglobin are Active In Vivo Purified human alpha chain, alpha-beta dimer or hemoglobin were tested in an in vivo assay as described in Example 15. As shown in Table 14, each of these were active at a concentration of 500 ng/mouse.

TABLE 14

| Treatment | % Kill |
|---|---|
| Control[1] | 49 |
| Human alpha chain | −22 |
| Human alpha-beta dimer | 14 |
| Human hemoglobin | −31 |

[1]Control - Bone marrow from testosterone-treated $BDF_1$ mice

EXAMPLE 18

Porcine INPROL is Active on Human Mononuclear or CD34+ Cord Blood Cells In Vitro In order to investigate the ability of purified INPROL from porcine bone marrow to affect cycling on human progenitors, umbilical cord blood cells were obtained. Either the total mononuclear cell fraction obtained after separation on Ficoll or the CD34+ fraction obtained after fractionation on anti-CD34 affinity columns (CellPro Inc.) was used. Cells were incubated for 48 hours in vitro in the presence of interleukin 3 (IL-3) and stem cell factor (SCF) (100 ng/ml each) in order to ensure that the early stem cells were in cycle. After this preincubation, cycling assays were conducted as described in Example 14 for the mouse except that CFU-GEMM (instead of CFU-MIX) were counted on Day 18 after plating. As shown in Table 15, porcine INPROL inhibited cycling of CFU-GEMM in either the bulk mononuclear cells or in the CD34+ fraction.

TABLE 15

| Treatment | % Kill |
|---|---|
| Mononuclear Cells | |
| Control | 93 |
| pINPROL[1] | 16 |
| CD34+Cells | |
| Control | 41 |
| pINPROL[1] | 21 |

[1]100 ng/ml

EXAMPLE 19

Purified Human Alpha Hemoglobin is Active on Human CFU-GEMM

Human umbilical cord blood mononuclear cells were obtained and incubated in IL-3 and SCF and used in a cycling assay as described in Example 18. As shown in Table 16, both porcine INPROL purified from bone marrow and human alpha hemoglobin, purified from peripheral blood, were active in this assay.

TABLE 16

| Treatment | % Kill |
|---|---|
| Control | 100 |
| pINPROL[1] | −6 |
| Human alpha chain[1] | −23 |

[1]100 ng/ml

EXAMPLE 20

Peptides obtained from Human Alpha Hemoglobin and from Human Beta Hemoglobin Sequences are Active To identify active peptide sequences, the three dimensional structure of myoglobin (which is inactive in this assay) was superimposed on the native three dimensional structure of the alpha chain present in adult human hemoglobin using a computer modeling program. Two peptides (representing amino acids 43–55 and 64–82, which are regions which are structurally different from myoglobin in three-dimensional space) were identified as having activity in the CFU-MIX cycling assay. In order to more closely approximate the loop found in the native alpha chain, a cyclic derivative of the 43–55 peptide (c43–55) (utilizing a disulfide bond) was also synthesized and found to be active.

The sequence of these peptides is as follows:

43–55 Phe-Pro-His-Phe-Asp-Leu-Ser-His-Gly-Ser-Ala-Gln-Val (SEQ ID NO:1)

c(43–55) Cys-Phe-Pro-His-Phe-Asp-Leu-Ser-His-Gly-Ser-Ala-Gln-Val-Cys (SEQ ID NO:2) (where the two Cys residues are disulfide-bonded)

64–82 Asp-Ala-Leu-Thr-Asn-Ala-Val-Ala-His-Val-Asp-Asp-Met-Pro-Asn-Ala-Leu-Ser-Ala (SEQ ID NO:3)

Two hemorphin sequences, hemorphin 10 (amino acids 32–41 of the beta chain sequence) and hemorphin 7 (amino acids 33–40) were tested and found to be active.

The sequences are as follows:

Hemorphin 10 Leu-Val-Val-Tyr-Pro-Trp-Thr-Gln-Arg-Phe (SEQ ID NO:26)

Hemorphin 7 Val-Val-Tyr-Pro-Trp-Thr-Gln-Arg (SEQ ID NO:27)

To test the activity of these sequences, the CFU-MIX cycling assay was conducted as described in Example 14. As shown in Tables 17–19, these peptides all are active in this assay.

TABLE 17

| Treatment | % Kill |
|---|---|
| Control | 47 |
| pINPROL[1] | 0 |
| Peptide (43–55) | |
| 100 ng/ml | 2 |
| 10 ng/ml | 18 |
| 1 ng/ml | 11 |

[1]100 ng/ml

TABLE 18

| Treatment | % Kill |
|---|---|
| Control | 43 |
| Peptide (43–55)[1] | 5 |
| Peptide (64–82)[1] | 9 |
| Hemorphin 10[1] | 1 |
| Hemorphin 7[1] | 0 |

[1]All peptides tested at 100 ng/ml

TABLE 19

| Treatment | % Kill |
|---|---|
| Control | 47 |
| Cyclic Peptide 43–55[1] | 0 |

[1]Tested at 100 ng/ml

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A peptide having the sequence Phe-Pro-His-Phe-Asp-Leu-Ser-His-Gly-Ser-Ala-Gln-Val (SEQ ID NO:1).

2. A cyclic peptide having the sequence Cys-Phe-Pro-His-Phe-Asp-Leu-Ser-His-Gly-Ser-Ala-Gln-Val-Cys (SEQ ID NO:2) where the two Cys residues form a disulfide bond.

3. A pharmaceutical composition comprising the peptide of claim 1.

4. A pharmaceutical composition comprising the peptide of claim 1 in unit dosage form.

5. A pharmaceutical composition comprising the peptide of claim 1, wherein the peptide concentration in said composition is 1 to 100 ng/ml.

6. A pharmaceutical composition comprising the peptide of claim 2.

7. A pharmaceutical composition comprising the peptide of claim 2 in unit dosage form.

* * * * *

UNITED STATES PATENT AND TRADEMARK OFFICE
CERTIFICATE OF CORRECTION

PATENT NO.    : 5,939,391
DATED         : August 17, 1999
INVENTOR(S)   : Tsyrlova et al.

Page 1 of 1

It is certified that error appears in the above-identified patent and that said Letters Patent is hereby corrected as shown below:

<u>Title page,</u>
Item [63] should read:

-- [63] Continuation-in-part of application No. 08/316,424, Sep. 30, 1994, which is a continuation-in-part of application No. PCT/US94/03349, Mar. 29, 1994, which is a continuation-in-part of application No. 08/040,942, Mar. 31, 1993, abandoned. --

Signed and Sealed this

Second Day of April, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 5,939,391
DATED        : August 17, 1999
INVENTOR(S)  : Tsyrlova et al.

It is certified that error appears in the above-identified patent and that said Letters Patent is hereby corrected as shown below:

<u>Column 7,</u>
Line 53, change "Tyr-Pro-Try-Gly-NH$_2$" to -- Tyr-Pro-Trp-Gly-NH$_2$ --.

Signed and Sealed this

Second Day of September, 2003

JAMES E. ROGAN
*Director of the United States Patent and Trademark Office*

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Phe Pro His Phe Asp Leu Ser His Gly Ser Ala Gln Val
    1               5                  10

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Cys Phe Pro His Phe Asp Leu Ser His Gly Ser Ala Gln Val Cys
    1               5                  10             15

(2) INFORMATION FOR SEQ ID NO:3:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Asp Ala Leu Thr Asn Ala Val Ala His Val Asp Asp Met Pro Asn Ala
    1               5                  10             15

Leu Ser Ala (2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Leu Val Val Tyr Pro Trp Thr Gln Arg Phe
    1               5                  10

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Leu Val Val Tyr Pro Trp Thr Gln Arg
    1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Leu Val Val Tyr Pro Trp Thr Gln
    1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Leu Val Val Tyr Pro Trp Thr
    1               5

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Leu Val Val Tyr Pro Trp
    1               5

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Leu Val Val Tyr Pro
    1               5

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Val Val Tyr Pro Trp Thr Gln
    1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Tyr Pro Trp Thr Gln Arg Phe
1               5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Tyr Pro Trp Thr Gln Arg
1               5
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Tyr Pro Trp Thr Gln
1               5
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Glu Glu Asp Cys Lys
1               5
```

(2) INFORMATION FOR SEQ ID NO:15:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GTGCTGTCTC CTGCCGACAA GACCAACGTC AAGGCCGCCT GGGGTAAGGT CGGCGCGCAC    60
```

```
GCTGGCGAGT ATGGTGCGGA GGCCCTGGAG AGGATGTTCC TGTCCTTCCC CACCACCAAG      120

ACCTACTTCC CGCACTTCGA CCTGAGCCAC GGCTCTGCCC AGGTTAAGGG CCACGGCAAG      180

AAGGTGGCCG ACGCGCTGAC CAACGCCGTG GCGCACGTGG ACGACATGCC CAACGCGCTG      240

TCCGCCCTGA GCGACCTGCA CGCGCACAAG CTTCGGGTGG ACCCGGTCAA CTTCAAGCTC      300

CTAAGCCACT GCCTGCTGGT GACCCTGGCC GCCCACCTCC CCGCCGAGTT CACCCCTGCG      360

GTGCACGCCT CCCTGGACAA GTTCCTGGCT TCTGTGAGCA CCGTGCTGAC CTCCAAATAC      420

CGT                                                                   423
```

(2) INFORMATION FOR SEQ ID NO:16:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Val Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140
```

(2) INFORMATION FOR SEQ ID NO:17:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GTGCACCTGA CTCCTGAGGA GAAGTCTGCC GTTACTGCCC TGTGGGGCAA GGTGAACGTG       60

GATGAAGTTG GTGGTGAGGC CCTGGGCAGG CTGCTGGTGG TCTACCTTTG ACCCAGAGG       120

TTCTTTGAGT CCTTTGGGGA TCTGTCCACT CCTGATGCTG TTATGGGCAA CCCTAAGGTG      180

AAGGCTCATG GCAAGAAAGT GCTCGGTGCC TTTAGTGATG GCCTGGCTCA CCTGGACAAC      240

CTCAAGGGCA CCTTTGCCAC ACTGAGTGAG CTGCACTGTG ACAAGCTGCA CGTGGATCCT      300

GAGAACTTCA GGCTGCTGGG CAACGTGCTG GTCTGTGTGC TGGCCCATCA CTTTGGCAAA      360

GAATTCACCC CACCAGTGCA GGCTGCCTAT CAGAAAGTGG TGGCTGGTGT GGCTAATGCC      420
```

```
CTGGCCCACA AGTATCAC                                                             438
```

(2) INFORMATION FOR SEQ ID NO:18:

(i) SEQUENCE CHARACTERISTICS:
        (A) LENGTH: 146 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

```
Val His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```

(2) INFORMATION FOR SEQ ID NO:19:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Val Leu Ser Gly Glu Asp Lys Ser Asn Ile Lys Ala Ala Trp Gly Lys
 1               5                  10                  15

Ile Gly Gly His Gly Ala Glu Tyr Gly Ala Glu Ala Leu Glu Arg Met
            20                  25                  30

Phe Ala Ser Phe Pro Thr Thr Lys Thr Tyr Phe Pro His Phe Asp Val
        35                  40                  45

Ser His Gly Ser Ala Gln Val Lys Gly His Gly Lys Lys Val Ala Asp
    50                  55                  60

Ala Leu Ala Ser Ala Ala Gly His Leu Asp Asp Leu Pro Gly Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ser His
            100                 105                 110
```

```
    His Pro Ala Asp Phe Thr Pro Ala Val His Ala Ser Leu Asp Lys Phe
        115                 120                 125

Leu Ala Ser Val Ser Thr Val Leu Thr Ser Lys Tyr Arg
        130                 135                 140

(2) INFORMATION FOR SEQ ID NO:20:

(i) SEQUENCE CHARACTERISTICS:
        (A) LENGTH: 146 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Val His Leu Thr Asp Ala Glu Lys Ala Val Ser Cys Leu Trp Gly
    1               5                   10                  15

Lys Val Asn Ser Asp Glu Val Gly Gly Glu Ala Leu Gly Arg Leu Leu
                    20                  25                  30

Val Val Tyr Pro Trp Thr Gln Arg Tyr Phe Asp Ser Phe Gly Asp Leu
                35                  40                  45

Ser Ser Ala Ser Ala Ile Met Gly Asn Ala Lys Val Lys Ala His Gly
        50                  55                  60

Lys Lys Val Ile Thr Ala Phe Asn Asp Gly Leu Asn His Leu Asp Ser
    65                  70                  75                  80

Leu Lys Gly Thr Phe Ala Ser Leu Ser Glu Leu His Cys Asp Lys Leu
                    85                  90                  95

His Val Asp Pro Glu Asn Phe Arg Leu Leu Gly Asn Met Ile Val Ile
                    100                 105                 110

Val Leu Gly His His Leu Gly Lys Asp Phe Thr Pro Ala Ala Gln Ala
                115                 120                 125

Ala Phe Gln Lys Val Val Ala Gly Val Ala Thr Ala Leu Ala His Lys
        130                 135                 140

Tyr His
    145

(2) INFORMATION FOR SEQ ID NO:21:

(i) SEQUENCE CHARACTERISTICS:
        (A) LENGTH: 141 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Val Leu Ser Ala Ala Asp Lys Ala Asn Val Lys Ala Ala Trp Gly Lys
    1               5                   10                  15

Val Gly Gly Gln Ala Gly Ala His Gly Ala Glu Ala Leu Glu Arg Met
                    20                  25                  30

Phe Leu Gly Phe Pro Thr Thr Lys Thr Tyr Phe Pro His Phe Asn Leu
                35                  40                  45

Ser His Gly Ser Asp Gln Val Lys Ala His Gly Gln Lys Val Ala Asp
        50                  55                  60

Ala Leu Thr Lys Ala Val Gly His Leu Asp Asp Leu Pro Gly Ala Leu
    65                  70                  75                  80

Ser Ala Leu Ser Asp Leu His Ala His Lys Leu Arg Val Asp Pro Val
                    85                  90                  95
```

```
    Asn Phe Lys Leu Leu Ser His Cys Leu Leu Val Thr Leu Ala Ala His
                100                 105                 110

His Pro Asp Asp Phe Asn Pro Ser Val His Ala Ser Leu Asp Lys Phe
            115                 120                 125

Leu Ala Asn Val Ser Thr Val Leu Thr Ser Lys Tyr Arg
    130                 135                 140
```

(2) INFORMATION FOR SEQ ID NO:22:

(i) SEQUENCE CHARACTERISTICS:
        (A) LENGTH: 146 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
    Val His Leu Ser Ala Glu Glu Lys Glu Ala Val Leu Gly Leu Trp Gly
    1               5                  10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45

Ser Asn Ala Asp Ala Val Met Gly Asn Pro Lys Val Lys Ala His Gly
    50                  55                  60

Lys Lys Val Leu Gln Ser Phe Ser Asp Gly Leu Lys His Leu Asp Asn
    65                  70                  75                  80

Leu Lys Gly Thr Phe Ala Lys Leu Ser Glu Leu His Cys Asp Gln Leu
                85                  90                  95

His Val Asp Pro Glu Asn Phe Arg Leu Leu Gly Asn Val Ile Val Val
                100                 105                 110

Val Leu Ala Arg Arg Leu Gly His Asp Phe Asn Pro Asp Val Gln Ala
            115                 120                 125

Ala Phe Gln Lys Val Val Ala Gly Val Ala Asn Ala Leu Ala His Lys
            130                 135                 140

Tyr His
    145
```

(2) INFORMATION FOR SEQ ID NO:23:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

```
    Val His Leu Ser Ala Glu Glu Lys Glu Ala Val Leu Gly Leu Trp Gly
    1               5                  10                  15

Lys Val Asn Val Asp Glu Val
                20
```

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS:
        (D) TOPOLOGY: linear

```
         (ii) MOLECULE TYPE: peptide (xi) SEQUENCE DESCRIPTION: SEQ ID NO:24:

Val Leu Ser Ala Ala Asp Lys Ala Asn Val Lys Ala Ala Trp Gly Lys
         1               5                   10                  15

Val Gly Gly Gln
                     20

(2) INFORMATION FOR SEQ ID NO:25:

(i) SEQUENCE CHARACTERISTICS:
              (A) LENGTH: 14 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:25:

Phe Pro His Phe Asn Leu Ser His Gly Ser Asp Gln Val Lys
         1               5                   10

(2) INFORMATION FOR SEQ ID NO:26:

(i) SEQUENCE CHARACTERISTICS:
              (A) LENGTH: 10 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:26:

Leu Val Val Tyr Pro Trp Thr Gln Arg Phe
         1               5                   10

(2) INFORMATION FOR SEQ ID NO:27:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:27:

Val Val Tyr Pro Trp Thr Gln Arg
         1               5
```